US007955800B2

(12) United States Patent
Chou et al.

(10) Patent No.: US 7,955,800 B2
(45) Date of Patent: Jun. 7, 2011

(54) METASTASIS-ASSOCIATED GENE PROFILING FOR IDENTIFICATION OF TUMOR TISSUE, SUBTYPING, AND PREDICTION OF PROGNOSIS OF PATIENTS

(75) Inventors: Yeh-Tze Chou, Taipei Hsien (TW); Harn-Jing Terng, Taipei Hsien (TW); Hsuan-Yu Chen, Taipei (TW); Sung-Liang Yu, Taipei (TW); Jeremy J. W. Chen, Fongyuan (TW); Pan-Chyr Yang, Taipei (TW)

(73) Assignee: Advpharma Inc., Taipei Hsien (TW)

( * ) Notice: Subject to any disclaimer, the term of this patent is extended or adjusted under 35 U.S.C. 154(b) by 1103 days.

(21) Appl. No.: 11/437,607

(22) Filed: May 22, 2006

(65) Prior Publication Data

US 2006/0211036 A1    Sep. 21, 2006

Related U.S. Application Data

(63) Continuation-in-part of application No. 10/180,637, filed on Jun. 25, 2002, now abandoned.

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. ....... 435/6; 435/91.1; 435/91.2; 435/91.51; 435/287.2; 536/23.1; 536/24.3; 536/24.33

(58) Field of Classification Search ............ 435/6, 91.1, 435/91.2, 91.51, 183, 287.2; 436/94, 501; 536/23.1, 24.3, 24.33
See application file for complete search history.

(56) References Cited

OTHER PUBLICATIONS

Hao et al., STAT1 and Survivin Expression in Full Lymph Node Examined Gastric Cancer by Using Tissue Microarray Technique. The Chinese-German Journal of Clinical Oncology, 5, 249-252, 2006.*
Sun et al., Gene expression prefiling on lung cancer outcome prediction: present clinical value and future premise. Cancer Epidemiol. Biomarkers Prev., 15, 2063-2068, 2006.*
Beane et al., Clinical impact of high-throughput gene expression studies in lung cancer. J. Thorac. Oncol., 4, 109-118, 2009.*
Newnham et al., Molecular profiling of non-small cell lung cancer: of what value in clinical practice? Heart, lung, and Circulation, 17, 451-462, 2008.*
Subramanian et al., Gene Expression-Based Prognostic Signatures in Lung Cancer: Ready for Clinical Use? Journal of National Cancer Institute, 102, 464-474, Apr. 2010.*
Taniwaki et al., Gene expression profiles of small-cell lung cancers: molecular signatures of lung cancer. International Journal of oncology, 29, 567-575, 2006.*
Ingersoll et al., Comparison of gene expression profiles between human and mouse monocyte subsets. eBlood, 115, e10-e19, 2010.*
Jemal et al., Cancer Statistics, 2005; CA Cancer Journal for Clinicians (2005) vol. 55, pp. 10-30.
Parkin et al., Cancer burden in the year 2000. The global picture; European Journal of Cancer (2001) vol. 37, pp. S4-S66.
Hoffman et al., Lung cancer; The Lancet, (2000), vol. 355, pp. 479-485.
Mountain, Revisions in the International System for Staging Lung Cancer; Chest (1997), vol. 111, pp. 1710-1717.
Naruke et al., Prognosis and survival in resected lung carcinoma based on the new international staging system; J Thora Cardiovasc Surg (1988), vol. 96, pp. 440-447.
Beer et al., Gene-expression profiles predict survival of patients with lung adenocarcinoma; Nature Medicine (2002), vol. 8, pp. 816-824.
Wigle et al., Molecular Profiling of Non-Small Cell Lung Cancer and Correlation with Disease-free Survival; Cancer Research (2002), vol. 62, pp. 3005-3008.
Ramaswamy et al., Translating Cancer Genomics into Clinical Oncology; N. Engl. J. Med. (2002), vol. 350, pp. 1814-1816.
Endoh et al., Prognostic Model of Pulmonary Adenocarcinoma by Expression Profiling of Eight Genes As Determined by Quantitative Real-Time Reverse Transcriptase Polymerase Chain Reaction; Journal of Clinical Oncology (2004), vol. 22, pp. 811-819.
Bhattacharjee et al., Classification of human lung carcinomas by mRNA expression profiling reveals distinct adenocarcinoma subclasses; Proc. Natl. Acad. Sci. (2001), vol. 98, pp. 13790-13795.
Garber et al., Diversity of gene expression in adenocarcinoma of the lung; Proc. Natl. Aca. Sci. (2001), vol. 98, pp. 13784-13789.
McDoniels-Silvers et al., Differential Gene Expression in Human Lung Adenocarcinomas and Squamous Cell Carcinomas; Clinical Cancer Research (2002), vol. 8, pp. 1127-1138.
McDoniels-Silvers et al., Differential Expression of Critical Cellular Genes in Human Lung Adenocarcinomas and Squamous Cell Carcinomas in Comparison to Normal Lung Tissues; Neoplasia (2002), vol. 4, pp. 141-150.
Nacht et al., Molecular characteristics of non-small cell lung cancer; Proc. Natl. Acad. Sci. (2001), vol. 98, pp. 15203-15208.
Chou et al., Mutation in the Tyrosine Kinase Domain of Epidermal Growth Factor Receptor Is a Predictive and prognostic Factor for Gefitinib Treatment in Patients with Non-Small Cell Lung Cancer; Clinical Cancer Research (2005), vol. 11, pp. 3750-3757.
Huang et al., High Frequency of Epidermal Growth Factor Receptor Mutations with Complex Patterns in Non-Small Cell Lung Cancers Related to Gefitinib Responsiveness in Taiwan; Clinical Cancer Research (2004), vol. 10, pp. 8195-8203.
Shigematsu et al., Clinical and Biological Features Associated with Epidermal Growth Factor Receptor Gene Mutations in Lung Cancers; Journal of the National Cancer Institute (2005), vol. 97, pp. 339-346.

(Continued)

*Primary Examiner* — Frank W Lu
(74) *Attorney, Agent, or Firm* — Hsiu-Ming Saunders; Intellectual Property Connections, Inc.

(57) ABSTRACT

Methods for determining a tumor in a human is disclosed. Also disclosed are methods for identifying adenocarcinoma, and methods for identifying squamous cell carcinoma in a human tumor sample. In addition, methods for predicting prognosis of metastasis and survival in a human having a tumor is disclosed.

16 Claims, 4 Drawing Sheets

OTHER PUBLICATIONS

Chen et al., Global Analysis of Gene Expression in Invasion by a Lung Cancer Model; Cancer Research (2001), vol. 61, pp. 5223-5230.

Chen et al., Profiling Expression Patterns and Isolating Differentially Expressed Genes by cDNA Microarray System with Colorimetry Detection; Genomcs (1998), vol. 51, pp. 313-324.

Chen et al., Tumor-Associated Macrophages: The Double-Edged Sword in Cancer Progression; Journal of Clinical Oncology (2005), vol. 23, pp. 953-964.

Bolstad et al., A comparison of normalization methods for high density oligonucleotide array data based on variance and bias; Bioinformatics (2003), vol. 19, pp. 185-193.

Benjamini et al., Controlling the False Discovery rate: A Practical and Powerful Approach to Multiple Testing; Journal of the Royal Statistical Society, Series B (1995), vol. 57, pp. 289-300.

Dudoit et al., Comparison of Discrimination Methods for the Classification of Tumors Using Gene Expression Data; Journal of the American Statistical Association (2002), vol. 97, pp. 77-87.

Bender et al., Caveolin-1 Levels Are Down-Regulated in Human Colon Tumors, and Ectopic Expression of Caveolin-1 in Colon Carcinoma Cell Lines Reduces Cell Tumorigenicity; Cancer Research (2000), vol. 60, pp. 5870-5878.

Ho et al., Up-Regulated Caveolin-1 Accentuates the Metastasis Capability of Lung Adenocarcinoma by Inducing Filopodia Formation; American Journal of Pathology (2002), vol. 161, pp. 1647-1656.

Sagara et al., Clinical significance of Caveolin-1, Caveolin-2 and HER2/neu mRNA expression in human breast cancer; British Journal of Cancer (2004), vol. 91, pp. 959-965.

Wiechen et al., Down-Regulation of Caveolin-1, a Candidate Tumor Suppressor Gene, in Sarcomas; American Journal of Pathology (2001), vol. 158, pp. 833-839.

Gouyer et al., Tissue Inhibitor of Metalloproteinase 1 Is an Independent Predictor of Prognosis in Patients with Nonsmall Cell Lung Carcinoma who Undergo Resection with Curative Intent; American Cancer Society (2005), vol. 103, pp. 1676-1684.

Spitz et al., Serum Insulin-like Growth Factor (IGF) and IGF-Binding Protein Levels and Risk of Lung Cancer: A Case-Control Study Nested in the β-Carotene and Retinol Efficacy Trial Cohort; Cancer Epidemiology, Biomarkers Prevention (2002), vol. 11, pp. 1413-1418.

Renehan et al., Insulin-like growth factor (IGF)-1, IGF binding protein-3, and cancer risk: systematic review and meta-regression analysis; The Lancet (2004), vol. 363, pp. 1346-1353.

Dudoit et al., Statistical Methods for Identifying Differentially Expressed Genes in Replicated cDNA Microarray Experiments; Statistica Sinica (2002), vol. 12, pp. 111-139.

Troyanskaya et al., Nonparametric methods for identifying differentially expressed genes in microarray data; Oxford University Press (2002), vol. 18, pp. 1454-1461.

Petty et al., Gene Expression Profiling in Non-Small Cell Lung Cancer: From Molecular Mechanisms to Clinical Application; Clinical Cancer Research (2004), vol. 10, pp. 3237-3248.

Poller et al., Production and Characterization of a Polyclonal Antibody to the c-*erb*B-3 Protein: examination of c-*erb*B-3 Protein Expression in Adenocarcinomas; Journal of Pathology (1992), vol. 168, pp. 275-280.

Sithanandam et al., Inactivation of ErbB3 by siRNA promotes apoptosis and attenuates growth and invasiveness of human lung adenocarcinoma cell line A549; Oncogene (2005), vol. 24, pp. 1847-1859.

Cox et al., Regression Models and Life-Tables; Journal of the Royal Statistical Society. Series B (1972), vol. 34, pp. 187-220.

Zhang et al., Recursive partitioning for tumor classification with gene expression microarray data; Proc. National Academy of Science (2001), vol. 98, pp. 6730-6735.

\* cited by examiner

METASTASIS-ASSOCIATED GENE PROFILING FOR IDENTIFICATION OF TUMOR TISSUE, SUBTYPING, AND PREDICTION OF PROGNOSIS OF PATIENTS

RELATED APPLICATION

This application is a Continuation-In-Part (CIP) of U.S. patent application Ser. No. 10/180,637, filed on Jun. 25, 2002, now abandoned, which is herein incorporated by reference.

FIELD OF THE INVENTION

The present invention relates to methods using a gene expression profiling analysis (1) to determine whether a human sample is a tumor using a gene set containing nucleic acid sequences of SEQ ID NOS: 1-7, 8-17 or 1-17; (2) to identify whether a tumor tissue is an adenocarcinoma (using a gene set containing nucleic acid sequences of SEQ ID NOS: 15, and 18-21) or a squamous cell carcinoma (using a gene set containing nucleic acid sequences of SEQ ID NOS: 22-27); and (3) to predict the prognosis of survival and metastasis in humans with tumor (using a gene set containing nucleic acid sequences of SEQ ID NOS:19, and 28-42 or SEQ ID NOS: 19, 29, 31, 40, and 41), particularly for those humans who are at the early stage of lung cancer. The gene expression profiling is preferably performed by cDNA microarray-based techniques and/or Real-Time Reverse Transcription-Polymerase Chain Reaction (Real-Time RT-PCR), and analyzed by statistical means.

BACKGROUND OF THE INVENTION

Cancer is a group of diseases characterized by uncontrolled growth and spread of abnormal cells. If the spread is not controlled, it can result in death. Cancer is caused by both external factors (i.e., tobacco, chemicals and radiation) and internal factors (inherited mutations, hormones, immune conditions and mutations that occur from metabolism). These causal factors may act together or in sequence to initiate or promote carcinogenesis. Ten or more years may often pass between exposure to external factors and detectable cancer. Cancer is treated by surgery, radiation, chemotherapy, hormones and immunotherapy.

All cancers involve the malfunction of genes that control cell growth and division. About 5% to 10% of all cancers are clearly hereditary, in that an inherited genetic alteration predisposes the person to a very high risk of particular cancers. The remainder of cancers are not hereditary, but result from damage to genes (mutations) that occur throughout one's lifetime, either due to internal factors, such as hormones or the digestion of nutrients within the cells, or external factors, such as tobacco, chemicals or sunlight.

Lung cancer is the most common cause of cancer death in the world (Jemal et al., *CA Cancer J. for Clin*. (2005) 55:10-30; Parkin et al., *European J. of Cancer* (2001) 37:S4-66). In 2005, lung cancer accounted for 13% of the cancer that was diagnosed. The incidence rate has been declining significantly in men, from a high of 102.1 per 100,000 in 1984 to 77.7 in 2001. In women, the rate decreased for the first time from 52.8 in 1998 to 49.1 in 2001, after a long period of increase.

Over 163,000 deaths due to lung cancer were reported in 2005. This accounts for approximately 29% of all cancer deaths. Since 1987, more women have died each year of lung cancer than from breast cancer. Death rates have continued to decline significantly in men since 1991 by about 1.9% per year. Female lung cancer death rates have recently reached a plateau after continuously increasing for several decades. Decreasing lung cancer incidence and mortality rates reflect decreased smoking rates over the past 30 years.

Cigarette smoking is by far the most important risk factor for lung cancer. Other risk factors include second hand smoke and occupational or environmental exposures to substances such as arsenic; some organic chemicals such as benzene; radon and asbestos; radiation exposure from occupational, medical, and environmental sources; air pollution and tuberculosis.

Cancers that begin in the lungs are divided into two major types, non-small cell lung cancer and small cell lung cancer, depending on how the cells look under a microscope. Each type of lung cancer grows and spreads in different ways and is treated differently. Non-small cell lung cancer is more common than small cell lung cancer, and it generally grows and spreads more slowly. There are three main types of non-small cell lung cancer. They are named for the type of cells in which the cancer develops: squamous cell carcinoma, adenocarcinoma and large cell carcinoma.

Squamous cell carcinoma is a cancer that begins in squamous cells, which are thin, flat cells that look like fish scales. Squamous cells are found in the tissue that forms the surface of the skin, the lining of the hollow organs of the body, and the passages of the respiratory and digestive tracts. Adenocarcinoma is a type of cancer that begins in cells that line certain internal organs and that have glandular (secretory) properties. Still further, large cell carcinoma is a type of cancer in which the cells are large and look abnormal in comparison to the surrounding cells when viewed under a microscope.

Lung cancer can also be classified as to where it is located before the actual type of cancer is identified. For example, lung cancer falls under the disease category of a neoplasm. A neoplasm is an abnormal mass of tissue that results when cells divide more than they should or do not die when they should. The neoplasm can then be further classified as thoracic neoplasms, respiratory tract neoplasms and lung neoplasms depending on where the cells are located. The difference between these locations has to do with definitively locating where the neoplasm exists. For example, a thoracic neoplasm exists in the chest region, a respiratory tract neoplasm includes all of the organs that are involved in breathing (i.e., the nose, throat, larynx, trachea, bronchi, and lungs) and a lung neoplasm is exclusively found in one of a pair of organs in the chest that supplies the body with oxygen, and removes carbon dioxide from the body.

Past efforts at early detection have not yet demonstrated the ability to reduce mortality. Chest x-ray, analysis of cells in sputum, and fiber optic examination of the of the bronchial passages have shown limited effectiveness in improving survival or determining prognosis. Newer tests, such as low-dose spiral computed tomography scans and molecular markers in the sputum, have produced promising results in detecting lung cancers at earlier, more operable stages, when survival is more likely. However, there are considerable risks associated with lung biopsy and surgery which must be considered when evaluating the risks and benefits of screening.

In addition, the current staging system of NSCLC is inadequate to predict outcome, when patients have the same clinical and pathological features. This is evident because approximately 30% of patients that present with NSCLC present with early stage disease and receive potentially curative treatment. However, up to 40% of these patients will relapse within 5 years (Hoffman et al., *Lancet* (2000) 355:

479-485; Mountain, *Chest* (1997) 111:1710-1717; and Naruke et al., *J. Thorac. Cardiovasc. Surg.* (1988) 96:440-447).

The introduction of molecular approaches deliver more information for identifying patients at high risk of recurrence or metastasis after resection, which might be improved by the management of NSCLC patients. Gene expression profiling has been shown to be able to classify patients with different survivals as demonstrated by Beer et al. (Beer et al., *Nat. Med.* (2002) 8:816-824 and Wigle et al., *Cancer Res.* (2002) 62:3005-3008). In addition, a considerable proportion of clinically early-staged patients were designated through gene expression profile as high-risk for poor prognosis. Nevertheless, clinical application of this gene profiling approach might be still limited by the enormity of the number of genes employed (Ramaswamy, *N. Engl. J. Med.* (2004) 350:1814-1816). Furthermore, most of genes selected for profiling were substantially heterogeneous across studies for lung cancer, with only very few genes being consistently included (Endoh et al., *J. Clin. Oncol.* (2004) 22:811-9).

In addition, several recent microarray studies revealed that gene expression profiles can be used to classify the subclasses of histopathological type of lung carcinomas (e.g., adenocarcinoma and SCC). (Bhattacharjee et al., *Proc. Natl. Acad. Sci.* (2001) 98:13790-13795; Garber et al., *Proc. Natl. Acad. Sci.* (2001) 98:13784-13789; McDoniels-Silvers et al., *Clin. Cancer Res.* (2002) 8:1127-1138; McDoniels-Silvers et al., *Neoplasia* (2002) 4:141-150; and Nacht et al., *Proc. Natl. Acad. Sci.* (2001) 98:15203-15208). Current data show that the optimal gene expression profile for discriminating subgroups of lung cancer might vary in different populations. For instance, the mutation rate of epidermal growth factor receptor (EGFR) in the populations of East Asian ethnicity (including Taiwan and Japan) have been found to have a higher response rate to treatment than other races (Chou et al., *Clin. Cancer Res.* (2005) 11:3750-7; Huang et al., *Clin. Cancer Res.* (2004) 10:8195-8203; Shigematsu et al., *J. Natl. Cancer Inst.* (2005) 97:339-346).

The inventors of the present invention have previously identified more than 600 genes as being metastasis associated. In the invention to be presented in the following sections, the authors further describe their findings of specific sets of genes which can determine the risk of developing a tumor in a human; identify the subclass of lung cancer, especially distinguishing adenocarcinoma from squamous cell carcinoma; and predict the prognosis of a human with a tumor.

SUMMARY OF THE INVENTION

The present invention provides (1) a method for determining whether a human sample is a tumor; (2) a method for identifying whether the tumor in the human is an adenocarcinoma and squamous cell carcinoma; and (3) a method for predicting the prognosis of a human having a tumor.

The first method requires a comparison of a gene expression of a gene set of a human sample to the corresponding gene expression of the same gene set in a control, which can be standardized data, a gene expression of the corresponding gene set in a healthy human subject, or a gene expression in a tissue of the normal area of the same human subject. The expression of the genes described herein is determined either by a real-time reverse transcription-polymerase chain reaction (RT-PCR) or by a cDNA microarray-based technique, which determines the gene expression based on a logarithmic intensity.

A 7-gene set and a 10-gene set have been selected for determination of whether the human sample is a tumor by a Wilcoxon signed-rank test. The gene expression of each gene in either the 7-gene set or the 10-gene set is compared to the corresponding gene expression in the control and further analyzed by a discriminant analysis and/or optionally a hierarchical clustering analysis. The 7-gene set includes THBS2 (SEQ ID NO:1), FAP (SEQ ID NO:2), IGFBP3 (SEQ ID NO:3), PLAU (SEQ ID NO:4), MCM4 (SEQ ID NO:5), MMP1 (SEQ ID NO:6), and CDC20 (SEQ ID NO:7). The genes in this group are characterized by their higher gene expression in the human tumor tissue than those of the control, preferably to be twice and significantly (i.e., with a p value of less than 0.05) higher than that of the control.

The 10-gene set includes ADARB1 (SEQ ID NO:8), THBD (SEQ ID NO:9), NR4A1 (SEQ ID NO:10), TGFBR2 (SEQ ID NO:11), SPARCL1 (SEQ ID NO:12), CAV1 (SEQ ID NO:13), ADRB2 (SEQ ID NO:14), K1AA1102 (SEQ ID NO:15), TGFBR3 (SEQ ID NO:16), and GPM6A (SEQ ID NO:17). The genes in this group are characterized by their lower gene expression in the human tumor tissue than those of the control, preferably to be twice lower and significantly (i.e., with a p value of less than 0.05) than that of the control.

Alternatively, a 17-gene set, which combines the 7-gene set and the 10-gene set, can also be used to determine the human tumor.

The human sample which can be used for determining the gene expression is preferably human tissue. The type of tumor that can be determined by this method includes, but is not limited to, respiratory tract neoplasm, thoracic neoplasm, lung cancer, adenocarcinoma, and squamous cell carcinoma.

The second method applies to determination of a subtype of lung cancer, i.e., an adenocarcinoma or a squamous cell carcinoma in a human sample which has been pre-determined to be tumorous. To determine whether the tumor tissue is an adenocarcinoma, a gene expression using a microarray-based technology of each gene in a 5-gene set in the human sample which has already been pre-determined to be tumorous has been identified. The 5-gene set includes MUC1 (SEQ ID NO:18), ErbB3 (SEQ ID NO:19), KIAA1102 (SEQ ID NO:15), PTPRU (SEQ ID NO:20), and SCP2 (SEQ ID NO:21). The 5-gene set is selected by a Wilcoxon rank sum test. The genes in this group are up regulated, preferably by more than 1.7 fold in gene expression, and significantly different (preferably with a significant coefficient p value of less than 0.05), in the human sample. The gene expression profile of the 5-gene set is performed by a cDNA microarray-based technology or a Real-Time RT-PCR further analyzed by a discriminant analysis and optionally a hierarchical clustering analysis.

To determine whether the sample is a squamous cell carcinoma, a 6-gene set in the human sample which has already been pre-determined to be tumorous has been selected by a Wilcoxon rank-sum test. This 6-gene set includes SLC43A3 (SEQ ID NO:22), MXD1 (SEQ ID NO:23), S100A8 (SEQ ID NO:24), ODC1 (SEQ ID NO:25), PIK3CA (SEQ ID NO:26), and CMKOR1 (SEQ ID NO:27). The genes in this group are up regulated, preferably by more than 1.7 fold, and significantly different (preferably with a significant coefficient p value of less than 0.05), in the human sample. The gene expression profile of the 6-gene set is performed by a cDNA microarray-based technology or a Real-Time RT-PCR and further analyzed by a discriminant analysis and optionally a hierarchical clustering analysis. The sequence in SEQ ID NO:22 can be replaced with SEQ ID NOS:44 and 45, which are in fact the same gene with slightly different length.

The third method applies to a prediction of the prognosis whether a human has a tumor, which includes obtaining a sample from the human and determining a gene expression of each gene in a 16-gene set. The 16-gene set includes ANXA5 (SEQ ID NO:28), LCK (SEQ ID NO:29), FRAP1 (SEQ ID NO:30), STAT1 (SEQ ID NO:31), NF1 (SEQ ID NO:32), HGF (SEQ ID NO:33), HMMR (SEQ ID NO:34), IRF4 (SEQ ID NO:35), ZNF264 (SEQ ID NO:36), ErbB3 (SEQ ID NO:19), STAT2 (SEQ ID NO:37), CPEB4 (SEQ ID NO:38), RNF4 (SEQ ID NO:39), DUSP6 (SEQ ID NO:40), MMD (SEQ ID NO:41), and DLG2 (SEQ ID NO:42). The individual gene expression of each gene in this 16-gene set can be used in combination with the regression coefficient for each gene to calculate a risk score, which has the following equation:

$$\begin{aligned}\text{Risk Score} = & -1.09 \times ANXA5 - 0.84 \times LCK - 0.77 \times FRAP1 - 0.58 \times STAT1 + \\ & 0.47 \times NF1 + 0.51 \times HGF + 0.52 \times HMMR + 0.52 \times IRF4 + \\ & 0.55 \times ZNF264 + 0.55 \times ErB3 + 0.59 \times STAT2 + 0.59 \times CPEB4 + \\ & 0.65 \times RNF4 + 0.75 \times DUSP6 + 0.92 \times MMD + 1.32 \times DLG2\end{aligned}$$

The risk score can be used to group the human into either a high-risk or a low-risk group for having the tumor.

Alternatively, a 5-gene set has been selected for predicting prognosis of a human having a tumor using real-time RT-PCR. This 5-gene set includes LCK (SEQ ID NO:29), STAT1 (SEQ ID NO:31), ErbB3 (SEQ ID NO:19), DUSP6 (SEQ ID NO:40), and MMD (SEQ ID NO:41), which is selected by a univariate Cox's proportional hazards regression analysis. The gene expression profile of this 5-gene set is analyzed by a decision tree model.

DETAILED DESCRIPTION OF THE INVENTION

Figure 1:
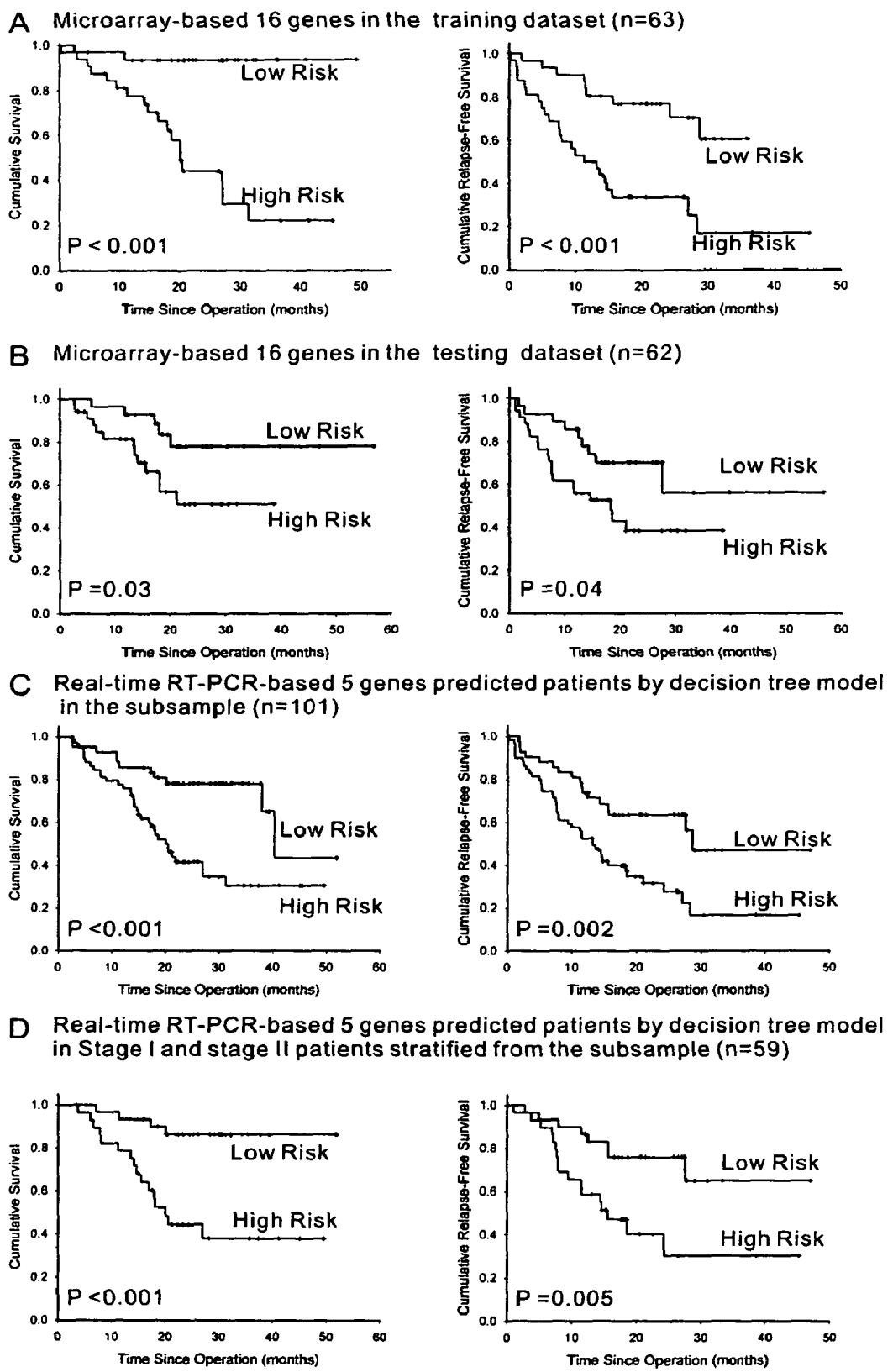
FIG. 1 shows Kaplan-Meier survival curves (overall survival for the left column and relapse-free survival for the right column) for the following four scenarios: (A) microarray-based 16 genes in the training dataset (n=63) with the median of risk score as the cut-off point for subgrouping; (B) microarray-based 16 genes in the testing dataset (n=62) using the same cut-off point derived from the training dataset; (C) real-time RT-PCR-based 5 genes predicted patients by decision tree model in the subsample (n=101); (D) real-time RT-PCR-based 5 genes predicted patients by decision tree model in Stage I and stage II patients stratified from the subsample (n=59).

One feature of this invention is to provide a method for determining whether the human sample is a tumor. Other features of this invention include a method of differentiating between two tumor types in a human and a method of predicting the prognosis of humans with a tumor. The tumors considered in this invention include thoracic neoplasms, respiratory tract neoplasms, lung neoplasms, lung cancer, non-small cell lung cancer, adenocarcinoma, and squamous cell carcinoma.

The method of determining whether the human sample is a tumor requires that a sample be taken from a human. The sample comprises tissue sample, which includes, but not limited to, epithelial tissue, connective tissue, muscle tissue and nervous tissue. The epithelial tissue samples include simple epithelia (i.e., squamous, cuboidal and columner epithelium), pseudo-stratified epithelia (i.e., columnar) and stratified epithelia (i.e., squamous). The connective tissue samples include embryonic connective tissue (i.e., mesenchyme and mucoid), ordinary connective tissue (i.e., loose and dense), and special connective tissue (i.e., cartilage, bone, and adipose). The muscle tissue sample include smooth (i.e., involuntary) and striated (i.e., voluntary and involuntary). The nervous tissue sample include neurons and supportive cells. In addition, the sample may contain cells unique to the pulmonary system, such as cells from the trachea, bronchi, bronchioli, and alveoli. Cells unique to the mouth and throat are also included such as all cell types exposed in the mouth that include cheek lining, tongue, floor and roof of the mouths, gums, throat as well as sputum samples.

The method also requires that a control, which is a normal sample, be taken from a human. The normal sample comprises tissue samples, such as epithelial tissue, connective tissue, muscle tissue and nervous tissue. The epithelial tissue samples include simple epithelia (i.e., squamous, cuboidal and columner epithelium), pseudo-stratified epithelia (i.e., columnar) and stratified epithelia (i.e., squamous). The connective tissue samples include embryonic connective tissue (i.e., mesenchyme and mucoid), ordinary connective tissue (i.e., loose and dense), and special connective tissue (i.e., cartilage, bone, and adipose). The muscle tissue sample includes smooth (i.e., involuntary) and striated (i.e., voluntary and involuntary). The nervous tissue sample includes neurons and supportive cells. In addition, the sample may contain cells unique to the pulmonary system, such as cells from the trachea, bronchi, bronchioli, and alveoli. Cells unique to the mouth and throat are also included such as all cell types exposed in the mouth that include cheek lining, tongue, floor and roof of the mouths, gums, throat as well as sputum samples.

The normal sample is defined as a sample expressing those genes that are included in Table 1 either from the same patient or from a healthy human subject. After the analytical model is defined, it becomes standardized data. By that time, it is only necessary to analyze the tumor sample from the patient rather than comparing the tumor sample to the normal sample.

Upon taking the sample from a human, the total RNAs are isolated and extracted from the specimen and are amplified. The amplification procedure is based on antisense RNA (aRNA) amplification, and involves a series of enzymatic reactions resulting in linear amplification of exceedingly small messenger RNA in array analysis. The procedure begins with total or poly(A) RNA that is reversely transcribed. After first-strand synthesis, the reaction is treated with RNase H to cleave the mRNA into small fragments. These small RNA fragments serve as primers during a second-strand synthesis reaction.

Once RNA is extracted from the sample, it is then converted to cDNA or cRNA in the procedure above in preparation for the microarray analysis, where the use of microarrays is to quantify mRNAs transcribed from different genes that encode different proteins. The copies may also be amplified by RT-PCR. Fluorescent tags or digoxigenin-dUTP are then enzymatically incorporated into the newly synthesized cDNA/cRNA or can be chemically attached to the new strands of DNA or RNA. A cDNA or cRNA molecule that contains a sequence complementary to one of the single-stranded probe sequences on the array is then hybridized, via base pairing (more at DNA), to the spot at which the complementary reporters are affixed. The spot is then fluoresced (or glowed) when examined using a microarray scanner.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Increased or decreased fluorescence intensity indicates that cells in the sample have recently transcribed, or ceased transcription, of a gene that contains the probed sequence ("recently," because cells tend to degrade RNAs soon after transcription). The intensity of the fluorescence is roughly proportional to the number of copies of a particular mRNA that were present and thus roughly indicates the activity or expression level of that gene. Arrays can paint a picture or "profile" of which genes in the genome are active in a particular cell type and under a particular condition that can be seen with the colorimetric assay.

The expressed gene sets to which this invention is directed are selected from those SEQ. IDs, Unigene Cluster numbers, Genbank Accession numbers, and GI numbers listed on Table 1 below.

TABLE 1[1]

| SEQ ID NO. | UNIGENE ID | GENE SYMBOL | ACCESSION NUMBER | GI NUMBER |
|---|---|---|---|---|
| 1 | HS.371147 | THBS2 | NM_003247 | GI:40317627 |
| 2 | HS.516493 | FAP | NM_004460 | GI:16933539 |
| 3 | HS.450230 | IGFBP3 | NM_000598 | GI:62243067 |

TABLE 1[1]-continued

| SEQ ID NO. | UNIGENE ID | GENE SYMBOL | ACCESSION NUMBER | GI NUMBER |
|---|---|---|---|---|
| 4 | HS.77274 | PLAU | NM_002658 | GI:53729348 |
| 5 | HS.460184 | MCM4 | NM_182746 | GI:33469916 |
| 6 | HS.83169 | MMP1 | NM_002421 | GI:13027798 |
| 7 | HS.524947 | CDC20 | NM_001255 | GI:4557436 |
| 8 | HS.474018 | ADARB1 | NM_015833 | GI:75709170 |
| 9 | HS.2030 | THBD | NM_000361 | GI:40288292 |
| 10 | HS.524430 | NR4A1 | NM_173157 | GI:27894343 |
| 11 | HS.82028 | TGFBR2 | NM_003242 | GI:67782323 |
| 12 | HS.62886 | SPARCL1 | NM_004684 | GI:21359870 |
| 13 | HS.74034 | CAV1 | NM_001753 | GI:15451855 |
| 14 | HS.591251 | ADRB2 | NM_000024 | GI:15718673 |
| 15 | HS.335163 | KIAA1102 | NM_014988 | GI:55741670 |
| 16 | HS.482390 | TGFBR3 | NM_003243 | GI:56682965 |
| 17 | HS.75819 | GPM6A | NM_201592 | GI:42476104 |
| 18 | HS.89603 | MUC1 | NM_002456 | GI:65301116 |
| 19 | HS.593522 | ErbB3 | NM_001982 | GI:54792099 |
| 20 | HS.19718 | PTPRU | NM_005704 | GI:19743934 |
| 21 | HS.476365 | SCP2 | NM_002979 | GI:56243511 |
| 22 | HS.99962 | SLC43A3 | NM_014096 | GI:46410928 |
| 23 | HS.468908 | MXD1 | NM_002357 | GI:70167417 |
| 24 | HS.416073 | S100A8 | NM_002964 | GI:21614543 |
| 25 | HS.467701 | ODC1 | NM_002539 | GI:4505488 |
| 26 | HS.478376 | PIK3CA | NM_006218 | GI:54792081 |
| 27 | HS.471751 | CMKOR1 | NM_020311 | GI:31083343 |
| 28 | HS.480653 | ANXA5 | NM_001154 | GI:4809273 |
| 29 | HS.470627 | LCK | NM_005356 | GI:20428651 |
| 30 | HS.338207 | FRAP1 | NM_004958 | GI:19924298 |
| 31 | HS.565365 | STAT1 | NM_007315 | GI:21536299 |
| 32 | HS.567266 | NF1 | NM_000267 | GI:4557792 |
| 33 | HS.396530 | HGF | NM_000601 | GI:58533168 |
| 34 | HS.72550 | HMMR | NM_012484 | GI:7108348 |
| 35 | HS.401013 | IRF4 | NM_002460 | GI:4505286 |
| 36 | HS.590962 | ZNF264 | NM_003417 | GI:55769562 |
| 37 | HS.530595 | STAT2 | NM_005419 | GI:38202247 |
| 38 | HS.127126 | CPEB4 | NM_030627 | GI:32698754 |
| 39 | HS.66394 | RNF4 | NM_002938 | GI:34305289 |
| 40 | HS.298654 | DUSP6 | NM_022652 | GI:42764686 |
| 41 | HS.463483 | MMD | NM_012329 | GI:52630444 |
| 42 | HS.503453 | DLG2 | NM_001364 | GI:91199537 |

TABLE 1[1]-continued

| SEQ ID NO. | UNIGENE ID | GENE SYMBOL | ACCESSION NUMBER | GI NUMBER |
|---|---|---|---|---|
| 43 | HS.590872 | TBP | NM_003194 | GI:61744433 |
| 44 | HS.99962 | SLC43A3 | NM_017611 | GI:40788008 |
| 45 | HS.99962 | SLC43A3 | NM_199329 | GI:41056258 |

[1]MCM4 includes GI:33469918 and GI:33469916; ADARB1 includes GI:75709171, GI:75709171, and GI:75709167; NR4A1 includes GI:27894343, GI:27894342, and GI:27894345; GPM6A includes GI:42476104, GI:42476106, and GI:42476107; MUC1 includes GI:33300664 and GI:65301116; PTPRU includes GI:19743930 and GI:19743932; STAT1 includes GI:21536299 and GI:21536300; HMMR includes GI:7108348 and GI:7108350; DUSP6 includes GI:42764686 and GI:4276482.

In order to determine whether the genes representing the tumor risk are present in a patient, the gene expression of a set of genes in a normal sample is compared to that of the sample taken from the patient. The gene set for determining the tumor sample is selected by a Wilcoxon signed-rank test. A 7-gene set, which includes THBS2 (SEQ ID NO:1), FAP (SEQ ID NO:2), IGFBP3 (SEQ ID NO:3), PLAU (SEQ ID NO:4), MCM4 (SEQ ID NO:5), MMP1 (SEQ ID NO:6), and CDC20 (SEQ ID NO:7); a 10-gene set, which includes ADARB1 (SEQ ID NO:8), THBD (SEQ ID NO:9), NR4A1 (SEQ ID NO:10), TGFBR2 (SEQ ID NO:11), SPARCL1 (SEQ ID NO:12), CAV1 (SEQ ID NO:13), ADRB2 (SEQ ID NO:14), K1AA1102 (SEQ ID NO:15), TGFBR3 (SEQ ID NO:16), and GPM6A (SEQ ID NO:17); and a 17-gene set (which combines the 7-gene set and the 10-gene set) are chosen for this study.

The normal sample can comprise those cells that possess expression characteristics that are not indicative of the presence of a tumor. In this manner, when the gene expression level is measured using the procedure as described above, if the intensity of the fluorescence probe from the microarray of the sample is greater than (for those genes that are up regulated in cancer tissue) or lower than (for those genes that are down regulated in cancer tissue) that of the normal sample, the chances for the patients to develop a tumor can be enhanced (fluorescent intensity comprises the scanned and quantified image of a colorimetric signal using specialized microarray analysis software such as GenPix Pro 5.0 (Axon Instruments)).

The normal sample is a term used to denote a control from a healthy subject or from the normal areas of the same patient, since it is the model against which the samples from the patients are compared. This control is based on the microarray intensities from such healthy subject that did not have genetic markers for tumorous conditions. In addition, after such a control model is established, standardized data can be obtained, and the gene expression level from the sample of a patient can be compared directly to the standardized data instead of the normal sample.

In determining whether a human has a tumor further requires that the gene expression level of those normal and potentially tumorous genes be compared to the control. When the genes are compared, those genes with a greater, or sometimes lower expression level will be considered as posing a risk to developing a tumor, depending upon the nature of the metastasis-associated genes. See Table 4 infra for details. Preferably, the expression level of those genes in the sample that may be designated as tumorous will have an expression level that is either twice elevated or twice suppressed than that of the normal sample.

In analyzing the genes selected, a Fisher discriminant analysis and/or a hierarchical clustering analysis are applied to construct gene profiles for the identification of tumor tissue.

Fisher Discriminant Analysis works by combining the variables in such a way that the differences between the predefined groups are maximized. Hierarchical Cluster Analysis is defined as grouping or segmenting a collection of objects into subsets or "clusters", such that those within each cluster are more closely related to one another than objects assigned to different clusters. In the hierarchical clustering analysis, the data are not partitioned into a particular cluster in a single step. Instead, a series of partitions takes place, which may run from a single cluster containing all objects to n clusters each containing a single object.

In differentiating between two tumor types, i.e., adenocarcinoma and squamous cell carcinoma, a tissue that has been pre-determined to be tumorous is obtained and a gene expression profiling analysis, using either microarray based technologies or real-time RT-PCR technology, for a selected set of genes is performed. The gene set is chosen by Wilcoxon rank-sum test. For identification of adenocarcinoma, a 5-gene set, which includes MUC1 (SEQ ID NO:18), ErbB3 (SEQ ID NO:19), KIAA1102 (SEQ ID NO:15), PTPRU (SEQ ID NO:20), and SCP2 (SEQ ID NO:21), is chosen. For identification of squamous cell carcinoma, a 6-gene set, which includes SLC43A3 (SEQ ID NO:22), MXD1 (SEQ ID NO:23), S100A8 (SEQ ID NO:24), ODC1 (SEQ ID NO:25), PIK3CA (SEQ ID NO:26), and CMKOR1 (SEQ ID NO:27), is selected. The genes that show at least about 1.7 fold up regulated and have a significant coefficient p value of less than 0.05 are chosen. The gene expression level is further analyzed by a discriminant analysis or a hierarchical clustering analysis.

The method of predicting prognosis of humans with a tumor requires that the tumor sample be subject to individual gene expression analysis for a chosen set of genes. A 16-gene set, which includes ANXA5 (SEQ ID NO:28), LCK (SEQ ID NO:29), FRAP1 (SEQ ID NO:30), STAT1 (SEQ ID NO:31), NF1 (SEQ ID NO:32), HGF (SEQ ID NO:33), HMMR (SEQ ID NO:34), IRF4 (SEQ ID NO:35), ZNF264 (SEQ ID NO:36), ErbB3 (SEQ ID NO:19), STAT2 (SEQ ID NO:37), CPEB4 (SEQ ID NO:38), RNF4 (SEQ ID NO:39), DUSP6 (SEQ ID NO:40), MMD (SEQ ID NO:41), and DLG2 (SEQ ID NO:42), has been selected. Alternatively, a 5-gene set has been selected for predicting prognosis of a human having a tumor using real-time RT-PCR. This 5-gene set includes LCK (SEQ ID NO:29), STAT1 (SEQ ID NO:31), ErbB3 (SEQ ID NO:19), DUSP6 (SEQ ID NO:40), and MMD (SEQ ID NO:41).

The intensity of those genes or gene sets are then quantified, thereby allowing the genes either in individually or in sets to be classified into a first set where the intensity is in the 0-25% range, a second set where the intensity is in the 25% or greater-50% range, a third set where the intensity is in the 50% or greater-75% range and a fourth set where the intensity is in the 75% or greater-100% range.

After classification of the gene sets, a univariate Cox's proportional hazards regression analysis is then performed for each gene thereby allowing the selection of overall survival associated genes. A risk score is then determined for the individual patients that comprise the summation of multiplying the regression coefficient of the selected gene by the corresponding expression intensity.

Cox regression (or proportional hazards regression) is a method for investigating the effect of several variables upon the time a specified event takes to happen. In the context of an outcome such as death this is known as Cox regression for survival analysis. The method does not assume any particular "survival model" but it is not truly non-parametric because it does assume that the effects of the predictor variables upon survival are constant over time and are additive in one scale.

Based on the median risk score, patients are then categorized as having a high or low-risk of surviving or having a relapse free survival. This is determined by a comparison to the corresponding Kaplan-Meier estimates of overall survival and relapse free survival. The Kaplan-Meier method is a nonparametric (actuarial) technique for estimating time-related events (the survivorship function). Ordinarily it is used to analyze death as an outcome. It may be used effectively to analyze time to an endpoint, such as remission. See FIG. 1.

As shown in FIG. 1, the Kaplan-Meier survival curves wherein overall survival is shown in the left column and relapse-free survival (relapse free survival is defined as the return of symptoms and signs of a disease such as a tumor after a period of improvement) is shown in the right column, represent the following four scenarios: (A) microarray-based 16 genes in the training dataset (n=63) with the median of risk score as the cut-off point for subgrouping; (B) microarray-based 16 genes in the testing dataset (n=62) using the same cut-off point derived from the training dataset; (C) real-time RT-PCR-based 5 genes predicted patients by decision tree model in the sub-sample (n=101); (D) real-time RT-PCR-based 5 genes predicted patients by Decision Tree Model in Stage I and stage II patients stratified from the sub-sample (n=59).

Figure 2:
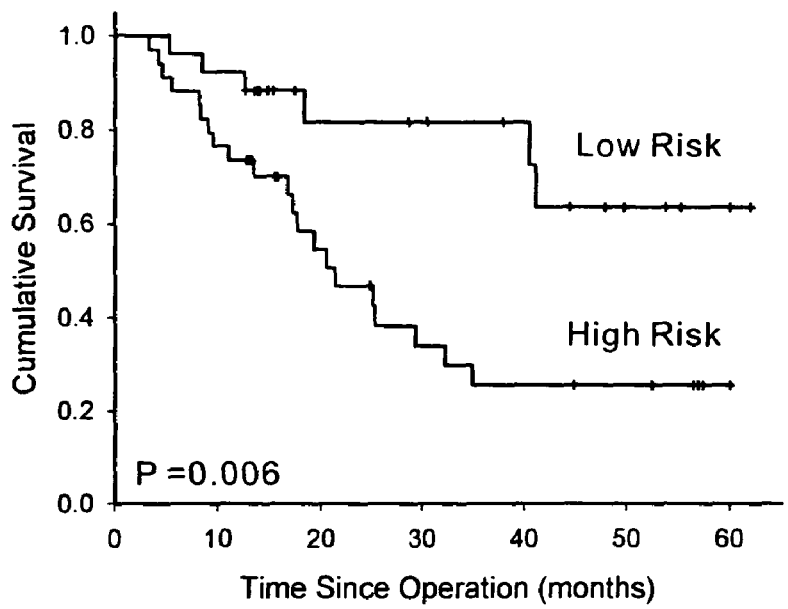
FIG. 2 shows Real-time RT-PCR-based 5 genes predictive model in the independent cohort (n=60) and Kaplan-Meier survival curves for overall survival. (A) Whole population of independent cohort (n=60); (B) Stage I and stage II patients stratified from the independent cohort (n=42).
Figure 2:
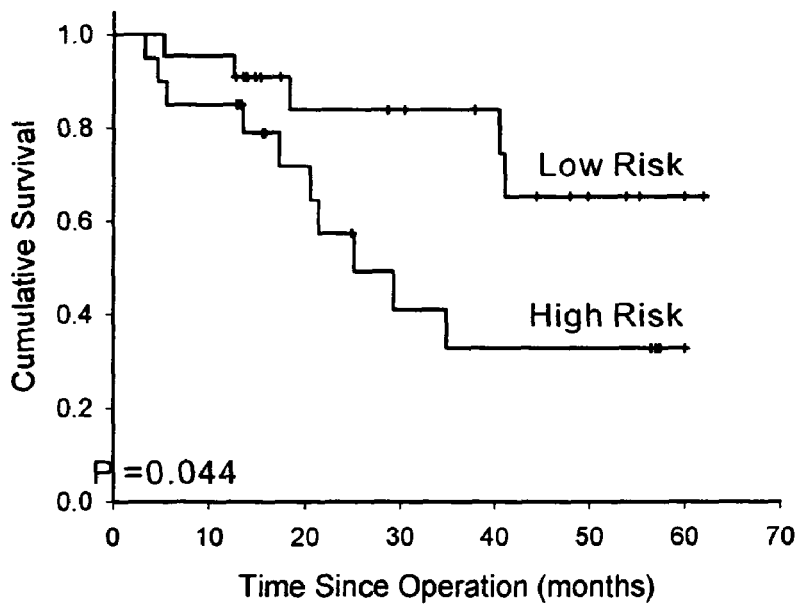

FIG. 2 further demonstrates a real-time RT-PCR-based 5 gene predictive model with an independent cohort (n=60) and Kaplan-Meier survival curves showing overall survival. The curve in (A) represents a whole population of independent cohort (n=60) and the curve in (B) represents stage I and stage II patients stratified from the independent cohort (n=42).

A Decision Tree is defined as taking input such as an object or situation described by a set of properties, and thereby outputting a yes/no decision. Decision Trees therefore represent Boolean functions. Functions with a larger range of outputs can also be represented. The Decision Tree considered in this invention is shown in FIG. 4.

Figure 4:
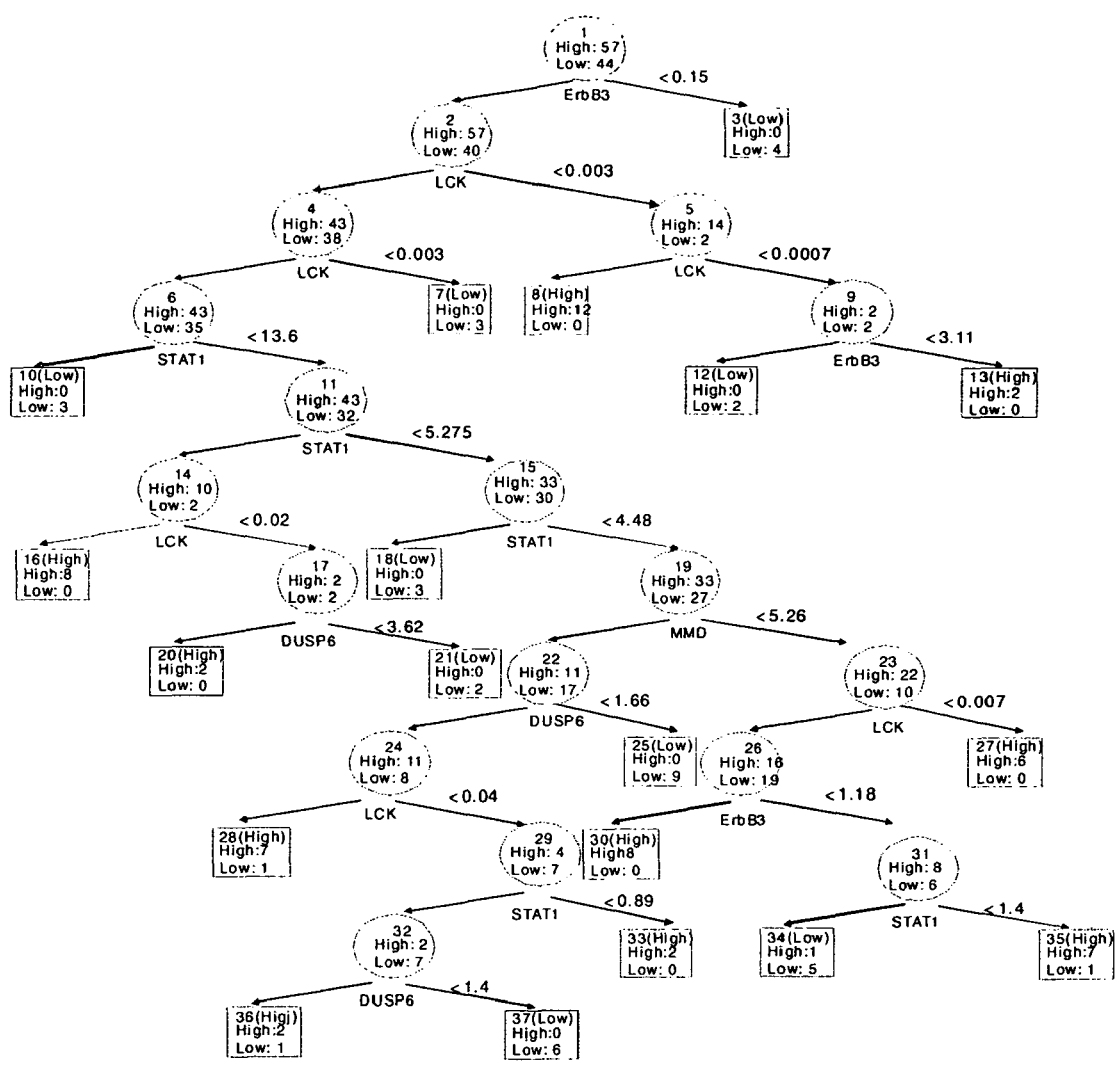
FIG. 4 shows a Decision Tree Model which was built on the basis of samples analyzed by real-time RT-PCR. Information in each node includes the node number (written on the top) and the sample number classified into high risk (as High indicated) and low risk (as Low indicated), which were classified by the prognosis prediction model using microarray assay data. Classification of a new sample (or specimen) is determined in which terminal node of the new sample (or specimen) would be contained. For instance, Node 1 contains the entire subset (101 relative gene expression measurements; 57 from High risk group and 44 from Low risk group). The first split is based on expression of "ErbB3" gene: relative gene expression measurement (by real-time RT-PCR) of less than 0.15 form node 3 and the other measurements form node 2.

The Decision Tree Model of FIG. 4 was built on the basis of samples analyzed by real-time RT-PCR. Information in each node includes the node number (written on the top) and the sample number classified into high risk (as High indicated) and low risk (as Low indicated), which were classified by the prognosis prediction model using microarray assay data. Classification of a new sample (or specimen) determines in which terminal node the new sample (or specimen) would be contained. For instance, Node 1 contains the entire subset (101 relative gene expression measurements; 57 from High risk group and 44 from Low risk group). The first split is based on expression of "ErbB3" gene: relative gene expression measurement (by real-time RT-PCR) of less than 0.15 form node 3 and the other measurements form node 2.

The following experimental designs are illustrative, but not limiting the scope of the present invention. Reasonable variations, such as those occur to reasonable artisan, can be made herein without departing from the scope of the present invention.

EXPERIMENTAL DESIGNS

Materials and Methods

1. Patients and Specimens

Lung tumor and adjacent normal tissue specimens were obtained from 188 patients who underwent surgical resection at the Taichung Veterans General Hospital from November 1999 to June 2004. The detailed clinicopathological features of the patients and tissues are shown in Table 2.

TABLE 2

| Clinicopathologic Characteristic of Patients (n = 188) | |
|---|---|
| Characteristic | No. of Patients (%) |
| Age | 65.8 ± 11.3 |
| Gender | |
| Male | 141 (75) |
| Female | 47 (25) |
| Stage | |
| I | 73 (39) |
| II | 36 (20) |
| III | 55 (29) |
| IV | 12 (6) |
| Not defined | 12 (6) |
| Primary Tumor | |
| T1 and T2 | 138 (73) |
| T3 and T4 | 46 (25) |
| Not defined | 4 (2) |
| Regional Lymph Nodes | |
| N0 | 90 (48) |
| N1, N2, and N3 | 83 (44) |
| Not defined | 15 (8) |
| Cell Type | |
| Adenocarcinoma | 101 (54) |
| Squamous cell carcinoma | 71 (38) |
| Others | 16 (8) |

2. Human cDNA Microarray Analysis

Human EST clones with the putative gene names were obtained from previous studies as described in Chen et al. (2001) (Chen et al., *Cancer Res.* (2001) 61:5223-5230), which is herein incorporated by reference. Each matrix on membrane array was constructed with 672 sequence-verified gene probes, consisting of 658 previously selected genes and 14 controls. GAPDH gene was used as positive control and spotted seven times on each matrix. Seven negative controls were gene fragments originating from plants. Every membrane contains two identical matrices and was used for hybridization analysis of one sample. Four micrograms of total RNA was isolated from the specimen and amplified using a RNA amplification kit (MessageAmp™ aRNA Kit, Ambion Inc., TX, USA), which subsequently was labeled with digoxigenin during reverse transcription as described in Chen et al. (1998). (Chen et al., *Genomics* (1998) 51:313-324). All of the assay procedures, including hybridization, color development, image analysis, and spot quantification, were performed as described in Chen et al. (1998, 2001 and 2005) (Chen et al., *Cancer Res.* (2001) 61:5223-5230; Chen et al., *Genomics* (1998) 51:313-324; and Chen et al., *J. Clin. Oncol.* (2005) 23:953-964).

3. Data Pretreatment

Step 1—Averaging Intensities

The average of two duplicated spots for each gene probe on every membrane microarray was obtained for next procedure.

Step 2—Normalization

The intensity average was rescaled using quantile normalization method, which is a method to make the distribution of probe intensities the same for every microarray. This process helped to normalize a set of chips to minimize non-biological differences that may exist, without choosing either a baseline chip to which all chips were normalized or working in a pairwise manner as described in Bolstad et al. (Bolstad et al., *Bioinformatics* (2003) 19:185-193).

Commercial microarray data software, such as Avadis, was used to process the quantile normalization and rescaling by ranking of all intensity data of each gene as described by Bolstad et al. and as shown in the Avadis™ user manual (Bolstad et al., *Bioinformatics* (2003) 19:185-193; Avadis™ (2004) Avadis™ user manual. USA, Strand Genomic Pvt Ltd.).

Step 3—Background Setting

The background intensity was reset at 3,000, when intensity data of the gene is less than or equal to 3,000, in order to identify noise signals derived from those insignificant genes as described by Chen et al. (2005) (Chen et al., *J. Clin. Oncol.* (2005) 23:953-964).

Step 4—Logarithmic Transformation

All pretreated data was then transformed by a logarithm with base 2.

Step 5—Filtration

The coefficient of variation (CV) of each gene was then calculated for filtering the insignificant genes. If the CV of a gene was less than 3%, the gene was then excluded from further analysis.

4. Data Grouping

Microarray data obtained from sample pairs, including tumor and adjacent normal tissue specimens, were randomly separated into training dataset and testing dataset before the statistical analysis. There were no significant differences in clinicopathologic features between these two sets for these three tasks, respectively. See Table 3.

TABLE 3

Summary of Clinicopathologic Features of Dataset

| Characteristic | Training Set No. of Patients (%) | Testing Set No. of Patients (%) | P value |
|---|---|---|---|
| (A) Identification of Cancer (n = 188 pairs) | | | |
| Age | 65.0 ± 11 | 66.5 ± 11 | 0.39[†] |
| Gender | | | |
| Male | 70 (74.5) | 71 (75.5) | 1.00[‡] |
| Female | 24 (25.5) | 23 (24.5) | |
| Stage | | | |
| I | 36 (40.9) | 37 (42.1) | 0.958[§] |
| II | 18 (20.5) | 18 (20.4) | |
| III | 27 (30.7) | 28 (31.8) | |
| IV | 7 (7.9) | 5 (5.7) | |
| Primary Tumor | | | |
| T1 and T2 | 64 (68.8) | 74 (81.3) | 0.06[‡] |
| T3 and T4 | 29 (31.2) | 17 (18.7) | |
| Regional Lymph Nodes | | | |
| N0 | 49 (54.4) | 41 (49.4) | 0.54[‡] |
| N1, N2, and N3 | 41 (45.6) | 42 (50.6) | |
| Cell Type | | | |
| Adenocarcinoma | 53 (56.4) | 48 (51.0) | 0.55[§] |
| Squamous cell carcinoma | 32 (34.0) | 39 (41.5) | |
| Others | 9 (9.6) | 7 (7.5) | |
| (B) Subtyping of Cancer (n = 172) | | | |
| Age | 64.9 ± 12 | 66.6 ± 11 | 0.30[†] |
| Gender | | | |
| Male | 64 (73.6) | 67 (78.8) | 0.48[‡] |
| Female | 23 (26.4) | 18 (21.2) | |
| Stage | | | |
| I | 30 (36.6) | 35 (44.9) | 0.54[§] |
| II | 20 (24.4) | 13 (16.7) | |
| III | 26 (31.7) | 26 (33.3) | |
| IV | 6 (7.3) | 4 (5.1) | |
| Primary Tumor | | | |
| T1 and T2 | 65 (75.6) | 60 (73.2) | 0.72[‡] |
| T3 and T4 | 21 (24.4) | 22 (23.8) | |
| Regional Lymph Nodes | | | |
| N0 | 37 (46.3) | 43 (55.1) | 0.27[‡] |
| N1, N2, and N3 | 43 (53.7) | 35 (44.9) | |
| Cell Type | | | |
| Adenocarcinoma | 51 (58.6) | 50 (58.8) | 1.00[‡] |
| Squamous cell carcinoma | 36 (41.40) | 35 (41.2) | |
| (C) Prediction of Survival and Metastasis (n = 125) | | | |
| Age | 65.9 ± 9.6 | 65.7 ± 9.6 | 0.56[†] |
| Gender | | | |
| Male | 48 (76.2) | 53 (85) | 0.26[‡] |
| Female | 15 (23.8) | 9 (14.5) | |
| Stage | | | |
| I | 25 (39.7) | 23 (37.1) | 0.08[§] |
| II | 10 (15.9) | 20 (32.3) | |
| III | 28 (44.4) | 19 (30.6) | |
| Primary Tumor | | | |
| T1 and T2 | 44 (69.8) | 46 (74.2) | 0.69[‡] |
| T3 and T4 | 19 (30.2) | 16 (25.8) | |
| Regional Lymph Nodes | | | |
| N0 | 27 (42.9) | 33 (53.2) | 0.28[‡] |
| N1, N2, and N3 | 36 (57.1) | 29 (46.8) | |
| Cell Type | | | |
| Adenocarcinoma | 34 (54) | 26 (41.9) | 0.21[‡] |
| Others | 29 (46) | 36 (58.1) | |

[†]T test
[‡]Fisher's exact test
[§]Chi-square test

Example 1

Genes for Identification of Tumor Tissue

1. Statistical Analysis

Microarray raw data was processed as described in the Data Pretreatment of the previous section. The logarithmic intensity was further normalized using the PROC RANK of the statistical software SAS (version 9.1; SAS Institute Inc., Cary, N.C., USA).

Microarray data obtained from tumor tissue and its adjacent normal tissue in each individual was then treated as paired data for statistical analysis. A Wilcoxon signed-rank test was used to select those genes with significant differences in expression level between the paired tissue as described in the Avadis™ user manual (Avadis™ user manual. (2004) USA, Strand Genomic Pvt Ltd.; and Rosner R. (2000) Fundamentals of biostatistics (ed 5). California, USA, Duxbury). A false discovery rate (FDR) was applied to calculate the corrected p values, in order to control the false positive rate at a nominal level of 0.05 (Benjamini and Hochberg, (1995) *J. the Royal Statistical Society. Series B* 57:289-300). Only those genes exhibiting a 2-fold difference in expression level were then included for the subsequent discriminant or cluster analysis.

On the basis of the genes selected above, both a supervised Fisher's discriminant analysis (Johnson and Wichern, (1998)

Applied multivariate statistical analysis (ed 4). New Jersey, USA, Prentice-Hall Inc.) and an unsupervised hierarchical clustering method (Draghici S. *Data analysis tools for DNA microarrays*. (2003) London, UK CRC Press) were applied to construct gene expression profiles for the identification of tumor tissue. A discriminant analysis is commonly known to one of ordinary skill in the statistical art to determine which variables discriminate between two or more naturally occurring groups. Although the performance of Fisher's discriminant analysis has been shown to be excellent in terms of distinction between tumor tissue and normal one when the number of genes is small (Dudoit et al., *J. American Statistical Association* (2002) 97:77-87), which is the case for this study, it cannot display the relations among these genes in an intuitive manner. For this purpose, a two-dimensional hierarchical clustering analysis using an average linkage method with a Pearson correlation coefficient proximity matrix (Draghici S. *Data analysis tools for DNA microarrays*. (2003) London, UK CRC Press) was further conducted.

2. Results

As shown in Table 4, seventeen genes were selected for identification of tumor or normal tissue (Table 4). All of them had higher expression level with at least a two-fold change either in tumor tissue (7 genes) or in normal tissue (10 genes).

In the training dataset, the results of the discriminant analysis showed that the validity indexes were as follows: sensitivity=0.90, specificity=0.96, positive prediction value (PPV)=0.96, and negative prediction value (NPV)=0.91. The derived model was further applied to the testing dataset to independently evaluate its validity. Analysis results revealed that all indexes remained high (sensitivity=0.86, specificity=0.89, PPV=0.89, and NPV=0.86). This indicates that this 17-gene set could clearly discriminate tumor tissues from normal ones very well.

On the other hand, when an unsupervised hierarchical clustering analysis using these selected genes was conducted in the training dataset (FIG. 4A), the color-gram also clearly indicated that most of the tissues with the same expression profile could be clustered together. There remained only a small number of specimens inconsistently alighted with the surrounding elements. A similar pattern was found in the testing dataset.

TABLE 4

Gene List for Classification Study: Identification of tumor tissue

| SEQ ID NO. | Gene Symbol | UniGene ID | Fold Change[†] | P Value[‡] |
|---|---|---|---|---|
| 1 | THBS2 | Hs.371147 | -2.5 | <0.001 |
| 2 | FAP | Hs.516493 | -2.2 | <0.001 |
| 3 | IGFBP3 | Hs.450230 | -2.2 | <0.001 |
| 4 | PLAU | Hs.77274 | -2.1 | <0.001 |
| 5 | MCM4 | Hs.460184 | -2.1 | <0.001 |
| 6 | MMP1 | Hs.83169 | -2.0 | <0.001 |
| 7 | CDC20 | Hs.524947 | -2.0 | <0.001 |
| 8 | ADARB1 | Hs.474018 | 2.0 | <0.001 |
| 9 | THBD | Hs.2030 | 2.1 | <0.001 |
| 10 | NR4A1 | Hs.524430 | 2.1 | <0.001 |
| 11 | TGFBR2 | Hs.82028 | 2.1 | <0.001 |
| 12 | SPARCL1 | Hs.62886 | 2.2 | <0.001 |
| 13 | CAV1 | Hs.74034 | 2.4 | <0.001 |
| 14 | ADRB2 | Hs.591251 | 2.5 | <0.001 |
| 15 | KIAA1102 | Hs.335163 | 2.5 | <0.001 |
| 16 | TGFBR3 | Hs.482390 | 2.6 | <0.001 |
| 17 | GPM6A | Hs.75819 | 2.6 | <0.001 |

[†]Negative values were up regulation in cancer tissue and positive values were up regulation in normal tissue.
[‡]P values were protected by FDR.

Several genes of the 17-gene set have been previously reported to be positively or negatively correlated with the occurrence of neoplasm, such as CAV1 (Bender et al., *Cancer Res.* (2000) 60:5870-5878; Ho et al., *Am. J. Pathol.* (2002) 161:1647-1656; Sagara et al., *Br. J. Cancer* (2004) 91:959-965; and Wiechen et al., *Am. J. Pathol.* (2001) 158:833-839), MMP1 (Gouyer et al., *Cancer* (2005) 103:1676-1684), and IGFBP3 (Spitz et al., *Cancer Epidemiol. Biomarkers Prev.* (2002) 11:1413-1418; and Renehan et al., *Lancet* (2004) 363:1346-1353).

Example 2

Genes for Subclassification of Lung Carcinomas

We further examined whether gene expression profile can be applied for distinguish different subtypes of lung carcinomas, especially two major types, adenocarcinomas and squamous cell carcinomas.

1. Statistical Analysis

Microarray raw data were processed as described in Data Pretreatment of the previous section. The logarithmic intensity was further normalized using the PROC RANK of the statistical software SAS (version 9.1; SAS Institute Inc., Cary, N.C., USA).

Only the intensity data obtained from tumor tissue specimens was randomly grouped into training dataset and testing dataset before the statistical analysis (Table 3 (B)). Wilcoxon rank-sum test, a non-parametric method for independent samples was processed, while 10,000 times of permutation was employed for gene selection (Rosner R. Fundamentals of biostatistics (ed 5). (2000) California, USA, Duxbury; Draghici S. *Data analysis tools for DNA microarrays*. (2003) London, UK, CRC Press; Dudoit et al., *Stat. Sin.* (2000) 12:111-139; and Troyanskaya et al., *Bioinformatics* (2002) 18:1454-1461). Two further criteria were set for gene selection, including a corrected p value that must be less than 0.05 and a difference in expression level higher than 1.7 fold.

2. Results

As shown in Table 5, eleven genes were selected for classification of lung cancer cell types. Among these eleven genes, five genes, which were KIAA1102 (SEQ ID NO:15), MUC1 (SEQ ID NO:18), ErbB3 (SEQ ID NO:19), PTPRU (SEQ ID NO:20), and SCP2 (SEQ ID NO:21), having negative value of fold change, were expressed with higher level in adenocarcinoma (AC). The other six genes, which were SLC43A3 (SEQ ID NO:22), MXD1 (SEQ ID NO:23), S100A8 (SEQ ID NO:24), ODC1 (SEQ ID NO:25), PIK3CA (SEQ ID NO:26), and CMKOR1 (SEQ ID NO:27), having positive value, in squamous carcinoma (SCC). This group of selected genes had at least a 1.7-fold change and p values less than 0.01.

In the training dataset, the discriminant analysis results showed that sensitivity and specificity was 0.81 and 0.82, respectively. PPV and NPV was 0.76 and 0.86, respectively. Similar results, regarding sensitivity, specificity, PPV, and NPV, were given in the testing dataset. This suggests that this 11-gene set could be applied for classification of AC and SCC type.

TABLE 5

Gene List for Classification Study: Subtyping

| SEQ ID NO. | Gene Symbol | UniGene ID | Fold Change[†] | P Value[‡] |
|---|---|---|---|---|
| 18 | MUC1 | Hs.89603 | -2.1 | .006 |
| 19 | ErbB3 | Hs.593522 | -2.0 | .006 |
| 15 | KIAA1102 | Hs.335163 | -1.8 | .008 |
| 20 | PTPRU | Hs.19718 | -1.8 | .006 |
| 21 | SCP2 | Hs.476365 | -1.7 | .008 |
| 22 | SLC43A3 | Hs.99962 | 1.7 | .006 |
| 23 | MXD1 | Hs.468908 | 1.7 | .006 |
| 24 | S100A8 | Hs.416073 | 1.8 | .008 |
| 25 | ODC1 | Hs.467701 | 1.8 | .008 |
| 26 | PIK3CA | Hs.478376 | 1.8 | .006 |
| 27 | CMKOR1 | Hs.471751 | 2.0 | .006 |

[†]Negative values were up regulation in adenocarcinoma (AC) and positive values were up regulation in squamous carcinoma (SCC).
[‡]P values were protected by FDR.

Specifically, one gene (noted as KIAA1102 (SEQ ID NO:15)) of the 11 genes selected for the subtyping of lung cancer was overlapped with those for the identification of tumor tissue. Some genes were reported to be excessively expressed in adenocarcinoma (AC), including MUC1 (SEQ ID NO:18) (surfactant-related and small airway-associated; Petty et al., *Clin. Cancer Res.* (2004) 10:3237-3248) and ErbB3 (a member of the EGFR family of tyrosine kinase; Poller et al., *J. Pathol.* 168:275-80, 1992; Sithanandam et al., *Oncogene* (2005) 24:1847-1859). The accuracy of the 11-gene set for the subtyping of lung cancer was not as good as that for the discrimination between normal and tumor tissues, which is probably not surprising given the task of subtyping being more difficult.

Example 3

Gene Expression Signatures to Predict Metastasis and Survival of Non-Small Cell Lung Cancer 1. Statistical Analysis Microarray raw data was processed as described in Data Pretreatment of the previous section. Only the intensity data obtained from tumor tissue specimens were randomly grouped into training dataset and testing dataset before the statistical analysis.

For the prediction of prognosis, the intensity of gene expression was coded as an ordinal level from 1 to 4, depending on the percentile of its intensity distributed in the range from the first (0-25%) the second (25%-50%), the third (50%-75%), or the fourth (75%-100%) range, respectively.

2. Selection of Survival-Associated Genes

Univariate Cox's proportional hazards regression analysis (Cox D R. Regression Models and Life-Tables. *Journal of the Royal Statistical Society Series B* (1972) 34:187-220) of individual gene was applied to selection of overall survival-associated genes. A Cox's regression coefficient of individual gene could be estimated and a group of genes with significant coefficient (p value<0.05) were selected. A risk score was given to each individual patient. This risk score was the summation of multiplication of the regression coefficient of selected gene with its corresponding expression intensity.

The median of all estimated risk scores obtained from the patients grouped in the training dataset was chosen as the cut-off value for classifying patients into high- versus low-risk group. The same cut-off value was directly applied to classification of patients grouped in the testing dataset for the same process.

Once the grouping of high- versus low-risk was determined, Kaplan-Meier method was used to generate for both overall and relapse-free survival curves. Differences in survival between the two groups were analyzed using log-rank test. The ability of independent prognostic factors was evaluated by multivariate Cox's proportional hazards regression analysis. The 0.05 significant level and two tailed p value was performed in this study.

3. Results

The experimental data obtained from 125 tumor tissue specimen, which had information on survival status, were applied to statistical analysis (Table 3(C)). The filtration of genes with a CV less than 3% resulted in reduction of gene number to 485 genes for further selection. Sixteen genes correlated with survival were selected on the basis of Cox proportional hazard regression analysis, in which 4 were protection genes (hazard ratio<1) and 12 risk genes (hazard ratio>1) (Table 6). The p values of all genes were less than 0.05.

TABLE 6

Genes Selected among 672 Genes for the Prediction of Survival and Metastasis

| SEQ ID NO. | Gene Symbol | UniGene ID | Hazard Ratio (p value)[†] | Correlation Between Microarray and Real-Time RT-PCR (p value)[‡] |
|---|---|---|---|---|
| 28 | ANXA5 | Hs.480653 | 0.34 (<0.01) | 0.06 (0.573) |
| 29 | LCK* | Hs.470627 | 0.43 (0.02) | 0.55 (<0.001) |
| 30 | FRAP1 | Hs.338207 | 0.46 (0.04) | -0.12 (0.239) |
| 31 | STAT1* | Hs.565365 | 0.56 (0.02) | 0.40 (<0.001) |
| 32 | NF1 | Hs.567266 | 1.60 (0.04) | -0.15 (0.123) |
| 33 | HGF | Hs.396530 | 1.66 (0.03) | 0.02 (0.818) |

TABLE 6-continued

Genes Selected among 672 Genes for the
Prediction of Survival and Metastasis

| SEQ ID NO. | Gene Symbol | UniGene ID | Hazard Ratio (p value)† | Correlation Between Microarray and Real-Time RT-PCR (p value)‡ |
|---|---|---|---|---|
| 34 | HMMR | Hs.72550 | 1.67 (0.04) | −0.03 (0.787) |
| 35 | IRF4 | Hs.401013 | 1.68 (0.03) | 0.06 (0.57) |
| 36 | ZNF264 | Hs.590962 | 1.73 (0.01) | 0.01 (0.949) |
| 19 | ErbB3* | Hs.593522 | 1.73 (0.03) | 0.59 (<0.001) |
| 37 | STAT2 | Hs.530595 | 1.80 (0.03) | 0.15 (0.122) |
| 38 | CPEB4 | Hs.127126 | 1.80 (0.02) | 0.16 (0.119) |
| 39 | RNF4 | Hs.66394 | 1.91 (0.02) | 0.13 (0.184) |
| 40 | DUSP6* | Hs.298654 | 2.12 (0.01) | 0.46 (<0.001) |
| 41 | MMD* | Hs.463483 | 2.50 (0.04) | 0.27 (0.006) |
| 42 | DLG2 | Hs.503453 | 3.75 (<0.01) | −0.09 (0.367) |

†Estimated by univariate Cox's proportional hazards regression analysis on the basis of microarray experiments.
‡Spearman rank correlation (n = 101).
*Genes selected in the final set for decision tree classification (see text)

These 16 genes were used to generate a risk score for every patient grouped in the training dataset. The risk score was calculated as follows:

Risk Score =

$-1.09 \times ANXA5 - 0.84 \times LCK - 0.77 \times FRAP1 - 0.58 \times STAT1 +$ $0.47 \times NF1 + 0.51 \times HGF + 0.52 \times HMMR + 0.52 \times IRF4 +$ $0.55 \times ZNF264 + 0.55 \times ErB3 + 0.59 \times STAT2 + 0.59 \times CPEB4 +$ $0.65 \times RNF4 + 0.75 \times DUSP6 + 0.92 \times MMD + 1.32 \times DLG$ Based on the median of risk score (cut-off), patients were categorized as high- or low-risk and their corresponding Kaplan-Meier estimates of overall survival and relapse-free survival were plotted in FIG. 1A, respectively. Patients with high-risk signatures had both a significantly poorer overall and relapse-free survival than those with low-risk signatures (p values<0.001, log rank test). As shown in the color-gram of the expression profiles for these selected genes (FIG. 4C), patients with higher risk scores expressed more risk genes (green), whereas those with lower risk scores expressed more protection genes (brown).

4. Transfer of Statistical Modeling of Training Dataset to Testing Dataset

Similar pattern in both the overall and relapse-free survival was obtained in comparing high- versus low-risk patients, when the same median risk score was applied as the cut-off point to the testing dataset, (FIG. 1B). Furthermore, patients with higher risk scores also expressed more risk genes (green) whereas those with lower risk scores expressed more protection genes (brown) (FIG. 4C).

Example 4

Genes for Prognosis Prediction Using Real-Time Reverse Transcription-Polymerase Chain Reaction Real-time Reverse Transcription Polymerase Chain Reaction (real-time RT-PCR) was applied to confirm the prognosis determination described in Example 3. Alternatively, a prediction model was also established using the assay data from real-time RT-PCR of 101 patients, which is in the sub-sample of 125 patients as mentioned in the Example 3.

1. Material and Methods

Sixteen genes selected for outcome prediction and one endogenous control gene, TATA-box binding protein (TBP), were analyzed. Gene-specific TaqMan® probes and primer sets were commercial purchased from Applied Biosystems (Hs00154054_m1 for ANXA5, Hs00265843_m1 for DLG2, Hs00185667_m1 for ZNF264, Hs00169257_m1 for DUSP6, Hs00286741_m1 for CPEB4, Hs0078427_m1 for LCK, Hs00234829_m1 for STAT1, Hs00231302_m1 for RNF4, Hs00180031_m1 for IRF4, Hs0013132_m1 for STAT2, Hs00300159_m1 for HGF, Hs00176538_m1 for ERBB3, Hs00169714_m1 for NF1, Hs00234508_m1 for FRAP1, Hs00202450_m1 for MMD, Hs00234864_m1 for HMMR, and Hs00427620_m1 for TBP). Real-time RT-PCR assays were carried out using Taqman One-Step RT-PCR Master Mix Reagent (Applied Biosystems, Branchburg, N.J.) on an ABI PRISM 7900HT Sequence Detection System, according to the manufacturer's instructions. Gene expression level was calculated as relative amount on the base of expression endogenous control gene, TBP, using Sequence Detector Software.

2. Statistical Analysis and Results
2.1. Correlation of Individual Gene Between Microarray and Real-Time RT-PCR Studies The consistency of two analysis approaches, microarray/Cox regression model and real-time RT-PCR, of these selected 16 genes (in Example 3) was further indexed by Spearman's rank correlation (Rosner R. *Fundamentals of biostatistics* (2000) (ed 5). California, USA, Duxbury). It is a method used for calculating correlation between variables, when the data does not follow the normal distribution. This is therefore a non-parametric test. Spearman's rank correlation coefficient, like all other correlation coefficient, will take a value between −1 and +1. A positive correlation is one in which the ranks of both variables increase together. A negative correlation is one in which the ranks of one variable increase as the ranks of the other variable decrease.

The expression level of five genes, including LCK (SEQ ID NO:29), STAT1 (SEQ ID NO:31), ErbB3 (SEQ ID NO:19), DUSP6 (SEQ ID NO:40), and MMD (SEQ ID NO:41), was significantly correlated between these two assays according to two criteria, such as Spearman's coefficient (positive and with greater value among 16 other genes) and p value<0.05 (Table 6). These 5 genes were dual specificity phosphatase 6 (DUSP6), monocyte to macrophage differentiation-associated (MMD), signal transducer and activator of transcription 1, 91 kD (STAT1), v-erb-b2 avian erythroblastic leukemia viral oncogene homolog 3 (ErbB3), and lymphocyte-specific protein tyrosine kinase (LCK). There are still 11 genes not showing gut correlation. This variation might very possible be resulted from two reasons. Firstly, from the experimental procedure point of view, an additional amplification procedure of total RNA was performed before hybridization for microarray approach, while the total RNA was directly applied for real-time RT-PCR. Another possible reason is that our ordinal coding for microarray assay might reduce the variance of gene expression and hence led to a decreased magnitude in correlation.

2.2. Prediction of Survival and Metastasis By Real-Time RT-PCR

Figure 3:
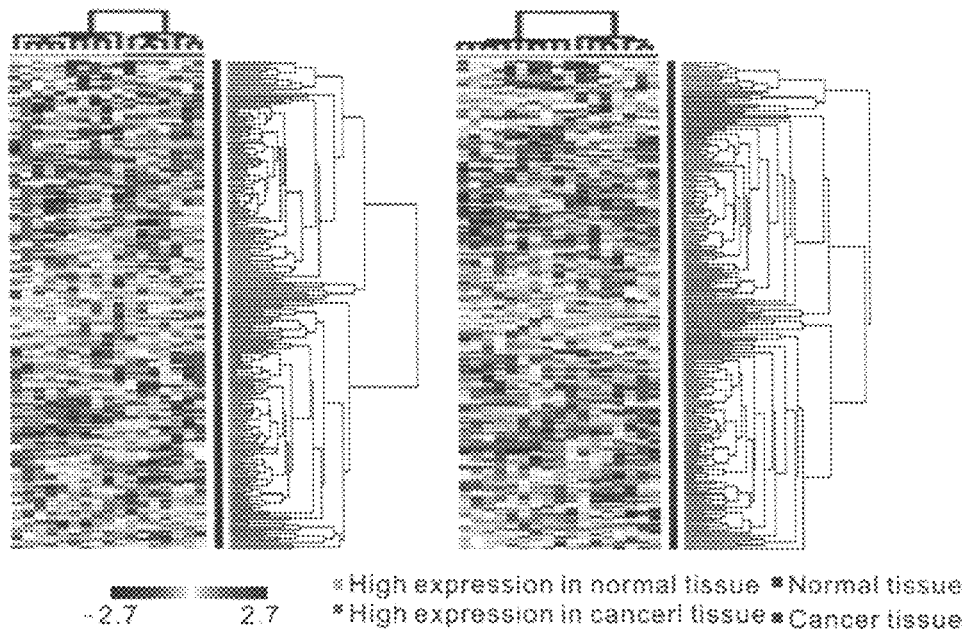
FIG. 3 shows color-gram (training dataset for the left column and testing dataset for the right column) for the following three scenarios and the two-dimensional hierarchical clustering analysis columns represented genes and rows represented specimens and represented the level of gene expression from blue (low) to red (high)) for (A) and (B): (A) 17 gene expression profiles for identification of cancer and the spectrum of normal distribution, from −2.7 to 2.7 arbitrary unit B 11 ene expression profiles for subtyping of cancer and the spectrum of normal distribution, from −2.4 to 2.4 (arbitrary unit); (C) 16 gene expression profiles for prediction of metastasis and survival, the white-to-red spectrum on the top represented the risk of patients from low to high, rows represented risk and protective genes, column represented patients, and the blue-to-red spectrum from −2.3 to 2.3 represented the levels of gene expression.
Figure 3:
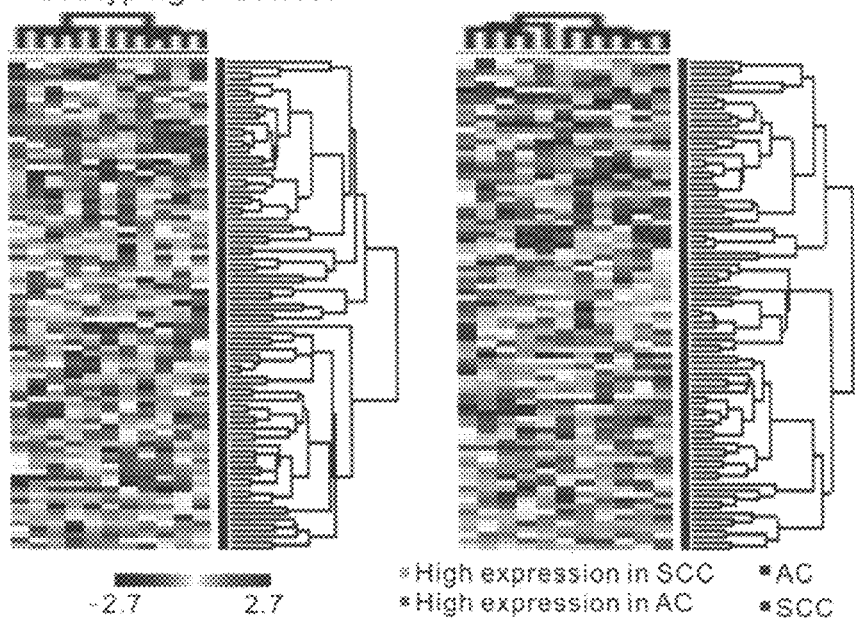
Figure 3:
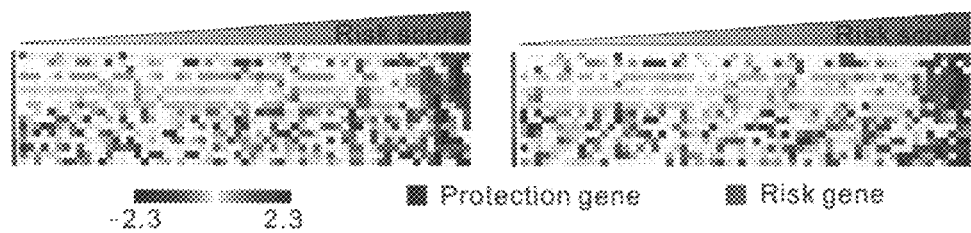

Expression levels of these 5 significant genes, measured by real-time RT-PCR assay, were applied to derive the Decision Tree classification model (FIG. 3) for prediction of the patient outcome being high-low risk. Classification trees have been used for classification of specimens using microarray gene expression profiles (Zhang et al., Proc. Nat. Acad. Sci. USA (2001) and Dudoit et al., J. Am. Stat. Assoc. (2002) 97:77-87). More information regarding the construction of classification tree is obtained from the reference written by Simon et al. (Statistic for Biology and Health-Design and Analysis of DNA Microarray Investigations (2003) Springer-Verlag, Chapter 8: 104-106):

Construction of a binary tree-structured classifier begins with a split of the gene expression profiles into two subsets (or nodes) based on the expression level of one of the genes. One subset consists of those samples with expression level of the selected gene above a selected threshold value, and the other subset consists of the remaining samples. After finding the gene and threshold value that optimally splits the set of samples of the training set into two subsets, the process in then repeated independently for each of the two resultant subsets. In other words, for each of the subsets, the gene and threshold value that best separates the samples in that subset are determined. This process of binary splitting of subsets results in a tree structure. Each node of the tree represents a set of samples. Each node is split based on a gene and a threshold expression level. Terminal nodes in the tree are assigned to a class. The rule for assigning a class to each terminal node is the basis for the classification of new samples.

Specifically, the decision tree model based on these 5 genes predicted patients well (overall accuracy=96%). On the basis of these 5 genes, patients with high-risk signatures remained to have both a significantly poorer overall (p value<0.001 for log rank test) and relapse-free survival (p value=0.002 for log rank test) than those with low-risk signatures (FIG. 1C).

TABLE 7

Summary of Clinicopathologic Features for Prediction of Survival and Metastasis Using Real-time RT-PCR assay data of five genes

| Characteristic | High No. of Patients (%) | Low No. of Patients (%) | P value |
|---|---|---|---|
| (A) Patients predicted by decision tree classification (n = 101) | | | |
| Age (mean ± SD) | 65 ± 11.6 | 66.3 ± 10.7 | 0.538[†] |
| Gender | | | |
| Male | 45 (76) | 35 (83) | 0.461[‡] |
| Female | 14 (24) | 7 (17) | |
| Stage | | | |
| I and II | 29 (49) | 30 (71) | 0.04[‡] |
| III | 30 (51) | 12 (29) | |
| Cell Type | | | |
| Adenocarcinoma | 36 (61.0) | 15 (36) | 0.016[‡] |
| Others | 23 (39.0) | 27 (64) | |

TABLE 7-continued

Summary of Clinicopathologic Features for Prediction of Survival and Metastasis Using Real-time RT-PCR assay data of five genes

| Characteristic | High No. of Patients (%) | Low No. of Patients (%) | P value |
|---|---|---|---|
| (B) Verification by the independent cohort (n = 60) | | | |
| Age (mean ± SD) | 69.4 ± 9.2 | 65.3 ± 10.3 | 0.108[†] |
| Gender | | | |
| Male | 30 (88) | 20 (77) | 0.305[‡] |
| Female | 4 (12) | 6 (23) | |
| Stage | | | |
| I and II | 20 (59) | 22 (85) | 0.046[‡] |
| III | 14 (41) | 4 (15) | |
| Cell Type | | | |
| Adenocarcinoma | 11 (32) | 13 (50) | 0.193[‡] |
| Others | 23 (68) | 13 (50) | |

[†]T test
[‡]Fisher's exact test

This 5-gene based dichotomization of high- versus low-risk was only associated with clinicopathological stage and histology (cell type), but not associated with age and gender (Table 7 (A)). To further assess whether this high-low risk dichotomy could predict clinical prognosis independently from the effect of age, gender, cell type, or clinicopathological stage, a multivariate Cox's proportional hazards regression analysis incorporating these variables as covariates was undertaken. As far as overall survival concerned, the hazard ratio for age (1.06, 95% CI=1.03 to 1.09, p value<0.001), for clinicopathological stage (2.13, 95% CI=1.16 to 3.93, p value=0.015), and for the high-low risk dichotomy (2.82, 95% CI=1.38 to 5.78, p value=0.005) remained significant. The hazard ratio for relapse-free survival remained significant for the clinicopathological stage (2.28, 95% CI=1.33 to 3.91, p value=0.003) and high-low risk dichotomy (1.92, 95% CI=1.06 to 3.46, p value=0.03).

2.3 Prognosis Prediction of Early-Staged Lung Cancer Patients

The further evaluation of the 5-gene-based high-low dichotomy for prognosis prediction of lung cancer patients in early stage was performed by conduction of Kaplan-Meier analysis in a sub-sample of patients with stage I or stage II (n=59). The results showed that both overall (p value<0.001, log rank test) and relapse-free survival (p value=0.005, log rank test) (FIG. 1D) have a good separation of patients with high- or low-risk. The percentage of early-staged patients that were assigned as high-risk by the 5-gene-based real-time RT-PCR was 47% (15 out of 32) for stage I patients and 52% (14 out of 27) for stage II patients, respectively.

2.4. Verification of the 5 Genes-Based Predictive Model in Independent Cohort

The verification of 5-gene predictive model was performed by analysis of an independent cohort (n=60). Patients with high-risk signatures remained to have a significantly poorer overall survival than those with low-risk signatures (p values=0.006 for log rank test) (FIG. 2A). This 5-gene based dichotomization of predicted high- versus low-risk was not associated with age, gender, histology (cell type), or clinicopathological stage (Table 7(B)).

A multivariate Cox's proportional hazards regression analysis incorporating these variables as covariates was undertaken, in order to further assess whether this predicted high-low risk dichotomy could predict clinical prognosis independently from the effect of age, gender, cell type, or clinicopathological stage. The hazard ratios for the predicted high-low risk dichotomy (3.36, 95% CI=1.35 to 8.35, p value=0.009) remained significant.

2.5 Prognosis Prediction of Early-Staged Lung Cancer Patients of Independent Cohort Additionally, a Kaplan-Meier analysis was conducted in a subsample of patients with stage I or stage II (n=42). The result showed that the patients were predicted high-risk with poorer overall survival (p values=0.044 for log rank test) (FIG. 2B). The percentage of early-stages patients that were assigned as predicted high-risk by the 5-gene-based real-time RT-PCR was 41% (12 out of 29) for stage I and 62% (8 out of 13) stage II patients, respectively.

2.6 Prognosis Prediction With Smaller Gene Number

Gene number for performing the prognosis prediction could be reduced without loss of much sensitivity and specificity. Table 8 shows five additional gene sets, each with three genes of five selected genes, could be applied to prediction with high accuracy, ranging from 0.91-0.93. The application of all smaller gene set shows with the sensitivity greater than 0.95 and with the specificity ranging from 0.86 to 0.95.

TABLE 8

Prognosis Prediction With Smaller Gene Number

| No. | Gene set | | | Predict | | Sensitivity | Specificity | Accuracy |
|---|---|---|---|---|---|---|---|---|
| 1 | Stat1 ErbB3 Lck | TRUE | H L | H 54 2 | L 3 42 | 0.95 | 0.95 | 0.95 |
| 2 | Stat1 ErbB3 Mmd | TRUE | H L | H 54 6 | L 3 38 | 0.95 | 0.86 | 0.91 |
| 3 | Stat1 ErbB3 Dusp6 | TRUE | H L | H 55 5 | L 2 39 | 0.96 | 0.89 | 0.93 |
| 4 | Lck ErbB3 Mmd | TRUE | H L | H 54 3 | L 3 41 | 0.95 | 0.93 | 0.94 |
| 5 | Lck ErbB3 Dusp6 | TRUE | H L | H 54 3 | L 3 41 | 0.95 | 0.93 | 0.94 |

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for predicting prognosis of survival in a human patient having non-small cell lung cancer, comprising the steps of:
   (a) obtaining a lung cancer tissue sample from the patient;
   (b) determining the expression intensity of each gene in a 16-gene set in the lung cancer tissue sample, wherein said 16-gene set comprises 16 genes consisting of annexin A5 (ANXA5; SEQ ID NO: 28), lymphocyte-specific protein tyrosine kinase (LCK; SEQ ID NO: 29), mechanistic target of rapamycin (FRAP1; SEQ ID NO: 30), signal transducer and activator of transcription 1 (STAT1; SEQ ID NO: 31), neurofibromin 1 (NF1; SEQ ID NO: 32), hepatocyte growth factor (HGF; SEQ ID NO: 33), hyaluronan-mediated motility receptor (HMMR; SEQ ID NO: 34), interferon regulatory factor 4 (IRF4; SEQ ID NO: 35), zinc finger protein 264 (ZNF264; SEQ ID NO: 36), v-erb-b2 avian erythroblastic leukemia viral oncogene homolog 3 (ErbB3; SEQ ID NO: 19), signal transducer and activator of transcription 2 (STAT2; SEQ ID NO: 37), cytoplasmic polyadenylation element binding protein 4 (CPEB4; SEQ ID NO:

38), ring finger protein 4 (RNF4; SEQ ID NO: 39), dual specificity phosphatase 6 (DUSP6; SEQ ID NO: 40), monocyte to macrophage differentiation-associated (MMD; SEQ ID NO:41), and discs, large (Drosophila) homolog 2 (DLG2; SEQ ID NO: 42);

(c) generating a risk score for said patient from the expression intensities of said 16 genes in the 16-gene set in the lung cancer tissue sample; and (d) predicting the prognosis of survival in the patient by comparing the risk score of the patient with a median of risk scores of a group of non-small cell lung cancer human patients, wherein the median of risk scores is generated from the expression intensities of said 16 genes in the lung cancer tissue samples of the group of non-small cell lung cancer human patients, the patient is predicted to have a poor chance of survival when the risk score of the patient is higher than the median of risk scores and the patient is predicted to have a good chance of survival when the risk score of the patient is lower than the median of risk scores.

2. The method according to claim 1, wherein the risk score of the patient is calculated using a univariate Cox's proportional hazards regression analysis based on a summation of the results generated by multiplying the expression intensity of each gene in the 16-gene set in the lung cancer tissue sample from the patient with the corresponding regression coefficient of each gene in the 16-gene set.

3. The method according to claim 2, wherein said risk score of the patient is calculated according to an equation:

$$\text{said risk score} = -1.09 \times [ANXA5] - 0.84 \times [LCK] - 0.77 \times [FRAP1] - 0.58 \times [STAT1] + 0.47 \times [NF1] + 0.51 \times [HGF] + 0.52 \times [HMMR] + 0.52 \times [IRF4] + 0.55 \times [ZNF264] + 0.55 \times [ErbB3] + 0.59 \times [STAT2] + 0.59 \times [CPEB4] + 0.65 \times [RNF4] + 0.75 \times [DUSP6] + 0.92 \times [MMD] + 1.32 \times [DLG2];$$

wherein [ANXA5], [LCK], [FRAP1], [STAT1], [NF1], [HGF], [HMMR], [IRF4], [ZNF264], [ErbB3], [STAT2], [CPEB4], [RNF4], [DUSP6], [MMD], and [DLG2] in the equation represent the expression intensities of ANXA5, LCK, FRAP1, STAT1, NF1, HGF, HMMR, IRF4, ZNF264, ErbB3, STAT2, CPEB4, RNF4, DUSP6, MMD, and DLG2 in the lung cancer tissue sample from the patient.

4. The method according to claim 1, wherein said 16-gene set in the lung cancer tissue sample from the patient is selected by a univariate Cox's proportional hazards regression analysis.

5. The method according to claim 1, wherein the expression intensity of each gene in the 16-gene set in the lung cancer tissue sample from the patient is determined by a cDNA microarray-based technology.

6. The method according to claim 1, wherein the expression intensity of each gene in the 16-gene set in the lung cancer tissue sample from the patient is determined by a real-time reverse transcription-polymerase chain reaction (RT-PCR) method.

7. A method for predicting prognosis of survival in a human patient having non-small cell lung cancer, comprising the steps of:
(a) obtaining a lung cancer tissue sample from the patient;
(b) measuring the expression intensity of each gene in a 5-gene set in the lung cancer tissue sample, wherein the 5-gene set comprises 5 genes consisting of LCK (SEQ ID NO: 29), STAT1 (SEQ ID NO: 31), ErbB3 (SEQ ID NO: 19), DUSP6 (SEQ ID NO: 40), and MMD (SEQ ID NO: 41); and
(c) predicting the prognosis of survival in the patient having the non-small cell lung cancer by applying the expression intensity of each gene in the 5-gene set in the lung cancer tissue sample from step (b) to a 5 gene-decision tree model constructed based on expression intensities of LCK, STAT1, ErbB3, DUSP6, and MMD in the lung cancer tissue samples from a group of non-small cell lung cancer human patients and determining whether the patient has a poor chance of survival or a good chance of survival.

8. The method according to claim 7, wherein the measuring step is performed by a real-time reverse transcription-polymerase chain reaction (RT-PCR) method and the expression intensity of each gene in the 5-gene set in the lung cancer tissue sample from the patient is calculated as a relative amount of expression intensity of an endogenous control gene.

9. The method according to claim 8, wherein the 5-gene decision tree model is a decision tree model according to FIG. 4.

10. The method of claim 8, wherein the endogenous control gene is a TATA box binding protein-encoding gene.

11. The method according to claim 7, wherein the expression intensity of each gene in the 5-gene set in the lung cancer tissue sample from the patient is measured by a cDNA microarray-based technology.

12. The method according to claim 7, wherein the human patient is at an early stage of the non-small cell lung cancer.

13. The method according to claim 7, wherein the 5-gene decision model is a decision tree model described in FIG. 4, and the human patient is at an early stage of the non-small cell lung cancer.

14. A method for predicting prognosis of survival in a human patient having non-small cell lung cancer, comprising the steps of:
(a) obtaining a lung cancer tissue sample from the patient;
(b) measuring the expression intensity of each gene in a 5-gene set in the lung cancer tissue sample, wherein the 5-gene set comprises 5 genes consisting of LCK (SEQ ID NO: 29), STAT1 (SEQ ID NO: 31), ErbB3 (SEQ ID NO: 19), DUSP6 (SEQ ID NO: 40), and MMD (SEQ ID NO: 41) by performing a real-time RT-PCR method and calculating the expression intensity of each gene in the 5-gene set in the lung cancer tissue sample from the patient as a relative amount of expression intensity of an endogenous control gene; and
(c) predicting the prognosis of survival in the patient having the non-small cell lung cancer by applying the expression intensity of each gene in the 5-gene set in the lung cancer tissue sample from step (b) to a 5 gene-decision tree model constructed based on expression intensities of LCK, STAT1, ErbB3, DUSP6, and MMD in the lung cancer tissue samples from a group of non-small cell lung cancer patients and determining whether the patient has a poor chance of survival or a good chance of survival.

15. The method according to claim 14, wherein the 5-gene decision tree model is a decision tree model according to FIG. 4.

16. The method according to claim 14, wherein the human patient is at an early stage of the non-small cell lung cancer.

* * * * *

SEQUENCE LISTING

```
<160> NUMBER OF SEQ ID NOS: 45

<210> SEQ ID NO 1
<211> LENGTH: 740
<212> TYPE: DNA
<213> ORGANISM: Homo sapiens
<220> FEATURE:
<221> NAME/KEY: misc_feature
<222> LOCATION: 654, 665, 685, 724
<223> OTHER INFORMATION: n = A,T,C or G

<400> SEQUENCE: 1
atttccacag gaaacagctt gaccatgatt acgccaagct tggcacgagg gaatactgtg      60
cataagccat tatgataaat taagcatgaa aaatattgct gaactacttt tggtgcttaa     120
agttgtcact attcttgaat tagagttgct ctacaatgac acacaaatcc cattaaataa     180
attataaaca agggtcaatt caaatttgaa gtaatgtttt agtaaggaga gattagaaga     240
caacaggcat agcaaatgac ataagctacc gattaactaa tcggaacatg taaaacagtt     300
acaaaaataa acgaactctc ctcttgtcct acaatgaaag ccctcatgtg cagtagagat     360
gcagtttcat caaagaacaa acatccttgc aaatgggtgt gacgcggttc cagatgtgga     420
tttggcaaaa cctcatttaa gtaaaaggtt agcagagcaa agtgcggtgc tttagctgct     480
gcttgtgccg ctgtggcgtc ggggaggctc ctgcctgagc ttccttccca gctttgctgc     540
ctgagaggaa ccagagcaga cgcacaggcc ggaaaaggcg catctaacgc gtatctaggc     600
tttggtaact gcggacaagt tgcttttacc tgatttgatg atcatttcat taaggtcca     660 gtatnaatat tttggtaata tttantaagt gactatagaa tgcaactcat ttaccaatac     720
ttantttaat atgcctagta                                                740
```

```
<210> SEQ ID NO 2
<211> LENGTH: 699
<212> TYPE: DNA
<213> ORGANISM: Homo sapiens
<220> FEATURE:
<221> NAME/KEY: misc_feature
<222> LOCATION: 3, 5, 424, 480, 481, 483, 585, 596, 599
<223> OTHER INFORMATION: n = A,T,C or G

<400> SEQUENCE: 2
aangnctggc ccttgcatct ggaactggtc ttttcaaatg tggtatagca gtggctccag      60
tctccagctg ggaatattac gcgtctgtct acacaggaga gattcatggg tctcccaaca     120
aaggatgata atcttgagca ctataagaat tcaactgtga tggcaagagc agaatatttc     180
agaaatgtag actatcttct catccacgga acagcagatg ataatgtgca ctttcaaaac     240
tcagcacaga ttgctaaagc tctggttaat gcacaagtgg atttccaggc aatgtggtac     300
tctgaccaga accacggctt atccggcctg tccacgaacc acttatacac ccacatgacc     360
cacttcctaa agcagtgttt ctctttgtca gactaaaaac gatgcagatg caagcctgta     420
tcanaatctg aaaaccttat ataaacccct cagacagttt gcttatttta ttttttatgn     480
ngnaaaatgc tagtataaac aaacaaatta atgttgttct aaaggctgtt aaaaaaaaga     540
tgaggactca gaagttcaag ctaaatattg tttacatttt ctggnctctg tgaaanaana     600
gaaaagggag tcatgcattt tgctttggac acagtgtttt atcacctgtt catttgaaga     660 aaataataa agtccgaagt tcaagtgcta aaaaaaaaa                             699

<210> SEQ ID NO 3
<211> LENGTH: 711
<212> TYPE: DNA
<213> ORGANISM: Homo sapiens
<220> FEATURE:
<221> NAME/KEY: misc_feature
<222> LOCATION: 597, 650, 662
<223> OTHER INFORMATION: n = A,T,C or G

<400> SEQUENCE: 3
gccaagaatt cggccgagga agaatgttct agggcactct gggaactata aaggcaggta      60
tttcgggccc tcctcttcag gaatcttcct gaagacatgg cccagtcgaa ggcccaggat     120
ggcttttgct gcggccccgt ggggtaggag ggacagagag acaggagag tcagcctcca     180 cattcagagg catcacaagt aatggcacaa ttcttcggat gactgcagaa aatagtgttt     240
tgtagttcaa caactcaaga cgaagcttat ttctgaggat aagctcttta aaggcaaagc     300 tttatttca tctctcatct tttgcctcct tagcacaatg taaaaaagaa tagtaatatc     360
agaacaggaa ggaggaatgg cttgctgggg agcccatcca ggacactggg agcacataga     420
gattcaccca tgtttgttga acttagagtc attctcatgc ttttctttat aattcacaca     480
tatatgcaga gaagatatgt tcttgttaac attgtataca acatagcccc aaatatagta     540
agatctatac tagataatcc tagatgaaat ggtagagatg ctatatgata caactgnggc     600
catgactgag gaaaggactc acgcccaaag actgggctgc tctcccggan gccaaaccca     660
anaaggctgg caaagtcagg ctcaaggaga ctctgcctgc tgcaaaacct t              711

<210> SEQ ID NO 4
<211> LENGTH: 696
<212> TYPE: DNA
<213> ORGANISM: Homo sapiens
<220> FEATURE:
<221> NAME/KEY: misc_feature
<222> LOCATION: 510, 656
<223> OTHER INFORMATION: n = A,T,C or G
```

<400> SEQUENCE: 4

```
aacgcagcaa cttgtctttt tctggactga agcctgcagg agttaaaaag ggcagggcat      60
ctcctgtgca tgggtgaagg gagagccagc tcccccgaac ggtgggcatt tgtgaggccc     120
atggttgaga aatgaataat ttcccaatta ggaagtgtaa cagctgaggt ctcttgaggg     180
agcttagcca atgtgggagc agcggtttgg ggagcagaga cactaacgac ttcagggcag     240
ggctctgata ttccatgaat gtatcaggaa atatatatgt ttgtgtatgt ttgcacactt     300
gtgtgtgggc tgtgagtgta agtgtgagta agagctggtg tctgattgtt aagtctaaat     360
atttccttaa actgtgtgga ctgtgatgcc acacagagtg gtctttctgg agaggttata     420
ggtcactcct ggggcctctt gggtccccca cgtgacagtg cctgggaatg tattattctg     480
cagcatgacc tgtgaccagc actgtctcan tttcactttc acatagatgt cccttttcttg    540
gccagttatc ccttcctttt aacctaattc atccaatcct cactgggtgg ggtgaggacc     600
actcctgtac actgaatatt tatatttcac tattttttatt tatatttttg gaattntaaa    660
taaaaagtga tcaataaaat gtgattttttc tgatga                              696
```

<210> SEQ ID NO 5
<211> LENGTH: 697
<212> TYPE: DNA
<213> ORGANISM: Homo sapiens
<220> FEATURE:
<221> NAME/KEY: misc_feature
<222> LOCATION: 503, 527, 562, 581, 584, 598, 602, 606, 608, 619, 627,
      628, 641, 646, 648, 661, 666, 674, 675, 684, 687, 688, 690
<223> OTHER INFORMATION: n = A,T,C or G

<400> SEQUENCE: 5

```
aatgagactc tgtccattgc aaaggctggg atcatctgtc agctcaatgc gcgcacctct      60
gtcctggcag cagcaaatcc cattgagtct cagtgggaaa tcctaaaaaa caaccattga     120
aaacatccag ctgcctcata ctttattatc aaggtttgat ttgatcttcc tcatgctgga     180
ccctcaggac gaagcctatg acaggcgtct ggctcaccac ctggtcgcac tgtactacca     240
gagcgaggag caggcagagg aggagctcct ggacatggcg gtgctaaagg actacattgc     300
ctacgcgcac agcaccatca tgccgcggct aagtgaggaa gccagccagg ctctcatcga     360
ggcttatgta gacatgagga agattggcag tagccgggga atggtttctg catacccctcg   420
acagctagag tcattaatcc gcttaacaga agcccatgct aaagtaagat tgtctaacaa     480
agttgaagcc cttgatgtgg aanaagccca acccctccat cgggaanctc tgaagcagtc     540
tgcaactgat ccccggactg gnatcgtgga catatttatt nttnctacgg ggatgagngc     600
cncctncnta aacggaaana aaaattnnct gaagcatttg naaaancnt ttttttttaa      660
ngggnaaac accnncttt aaanacnncn acttttt                                697
```

<210> SEQ ID NO 6
<211> LENGTH: 640
<212> TYPE: DNA
<213> ORGANISM: Homo sapiens
<220> FEATURE:
<221> NAME/KEY: misc_feature
<222> LOCATION: 1, 532, 557, 599, 603, 606, 609, 614, 616, 619, 625
<223> OTHER INFORMATION: n = A,T,C or G

<400> SEQUENCE: 6

```
naagccaaga attcggcacg aggacgattc ggggagaagt gatgttcttt aagacagatt      60
ctacatgcgc acaaatccct tctacccgga agttgagctc aatttcattt ctgttttctg     120
```

| | |
|---|---|
| gccacaactg ccaaatgggc ttgaagctgc ttacgaattt gccgacagag atgaagtccg | 180 |
| gttttcaaa gggaataagt actgggctgt tcagggacag aatgtgctac acggataccc | 240 |
| caaggacatc tacagctcct ttggcttccc tagaactgtg aagcatatcg atgctgctct | 300 |
| ttctgaggaa aacactggaa aaacctactt ctttgttgct aacaaatact ggaggtatga | 360 |
| tgaatataaa cgatctatgg atccaggtta tcccaaaatg atagcacatg actttcctgg | 420 |
| aattggccac aaagttgatg cagttttcat gaaagatgga ttttttctatt tctttcatgg | 480 |
| aacaagacaa tacaaatttg atcctaaaac gaaaaaatt ttgactctcc anaaagctaa | 540 |
| tagctgggtc aactgcngga aaaattgaca ttctaatttg aatggaaaac acatggggng | 600 |
| agnccnaana aggngnttnc tgaanaactg gctattttct | 640 |

<210> SEQ ID NO 7
<211> LENGTH: 738
<212> TYPE: DNA
<213> ORGANISM: Homo sapiens
<220> FEATURE:
<221> NAME/KEY: misc_feature
<222> LOCATION: 738
<223> OTHER INFORMATION: n = A,T,C or G

<400> SEQUENCE: 7

| | |
|---|---|
| aatttccaca ggaaacagct atgacatgat tacgaattta atacgactca ctatagggaa | 60 |
| tttggccctc gaggccaaga attcggcacg agcagcctga aaacagccag acgcccacca | 120 |
| agaaggaaca tcagaaagcc tgggctttga acctgaacgg ttttgatgta gaggaagcca | 180 |
| agatccttcg gctcagtgga aaaccacaaa atgcgccaga gggttatcag aacagactga | 240 |
| aagtactcta cagccaaaag gccactcctg gctccagccg gaagacctgc cgttacattc | 300 |
| cttccctgcc agaccgtatc ctggatgcgc ctgaaatccg aatgactat tacctgaacc | 360 |
| ttgtggattg gagttctggg aatgtactgg ccgtggcact ggacaacagt gtgtacctgt | 420 |
| ggagtgcaag ctctggtgac atcctgcagc ttttgcaaat ggagcagcct ggggaatata | 480 |
| tatcctctgt ggcctggatc aaagagggca actacttggc tgtgggcacc agcagtgctg | 540 |
| aggtgcagct atgggatgtg cagcagcaga acggcttcg aaatatgacc agtcactctg | 600 |
| cccgagtggg ctccctaagc tggaacagct atatcctgtc cagtggttca cgttctggcc | 660 |
| cattcaccac catgatgttc gggtagcaaa acaccatgtg ggcacactga tgggcacagc | 720 |
| caggaaatgt gtggcttn | 738 |

<210> SEQ ID NO 8
<211> LENGTH: 757
<212> TYPE: DNA
<213> ORGANISM: Homo sapiens
<220> FEATURE:
<221> NAME/KEY: misc_feature
<222> LOCATION: 384, 745
<223> OTHER INFORMATION: n = A,T,C or G

<400> SEQUENCE: 8

| | |
|---|---|
| agcaggtggt ctgccccagg cataaagaag gaaattggcc atctttccca cctctaaatt | 60 |
| ctgtaaaatt atagacttgc tcaaaagatt ccttttgatc atccccacgc tgtgtaagtg | 120 |
| gaaagggcat tgtgttccgt gtgtgtccag tttacagcgt ctctgccccc tagcgtgttt | 180 |
| tgtgacaatc tccctgggtg aggagtgggt gcacccagcc ccgaggccag tggttgctcg | 240 |
| gggccttccg tgtgagttct agtgttcact tgatgccggg gaatagaatt agagaaaact | 300 |
| ctgacctgcc gggttccagg gactggtgga ggtggatggc aggtccgact cgaccatgac | 360 |

```
ttagttgtaa gggtgtgtcg gctnttccag tctcatgtga aaatcctcct gtctctggca      420
gcactgtctg cactttcttg tttactgttt gaagggacga gtaccaagcc acaagaacac      480
ttcttttggc cacagcataa gctgatggta tgtaaggaac cgatgggcca ttaaacatga      540
actgaacggt taaaagcaca gtctatggaa cgctaatgga gtcagcccct aaagctgttt      600 gcttttttcaa gctttggatt acatgctttt aatttgattt tagaatctgg acactttcta    660
tgaatgtaat tcggctgaga aaacatgtgc tgagatgcaa tcctcagtgt tctctgtatg      720
taaatctgtg tatacaccac acgtnacaac tgcatga                              757
```

```
<210> SEQ ID NO 9
<211> LENGTH: 735
<212> TYPE: DNA
<213> ORGANISM: Homo sapiens
<220> FEATURE:
<221> NAME/KEY: misc_feature
<222> LOCATION: 625, 735
<223> OTHER INFORMATION: n = A,T,C or G

<400> SEQUENCE: 9
atttccacag gaaacagcta tgacatgatt acgaatttaa taccgactca ctatagggaa       60
tttggccctc gaggccaaga attcggcacg agaaacacct cccaggagac agttcaagaa      120
agcttcaaac tgcatgattc atgccaatta gcaattgact gtcactgttc cttgtcactg      180
gtagaccaaa ataaaaccag ctctactggt cttgtggaat gggagcttg ggaatggatc       240 ctggaggatg cccaattagg gcctagcctt aatcaggtcc tcagagaatt tctaccattt      300
cagagaggcc ttttggaatg tggcccctga acaagaattg gaagctgccc tgcccatggg     360
agctggttag aaatgcagaa tcctaggctc cacccatcc agttcatgag aatctatatt       420
taacaagatc tgcagggggt gtgtctgctc agtaatttga ggacaaccat tccagactgc      480
ttccaatttt ctggaataca tgaaatatag atcagttata agtagcaggc caagtcaggc     540
ccttattttc aagaaactga ggaattttct ttgtgtagct ttgctctttg gtagaaaagg    600
ctaggtacac agctctagac actgnccaca gggtctgcaa ggctttggtt cagctaacta     660
ggaatgaaat cctgcttcag tgtatggaaa taaatgtatc atagaaatgt aacttttgta     720
agacaaaagg tttcn                                                     735
```

```
<210> SEQ ID NO 10
<211> LENGTH: 731
<212> TYPE: DNA
<213> ORGANISM: Homo sapiens
<220> FEATURE:
<221> NAME/KEY: misc_feature
<222> LOCATION: 550, 666
<223> OTHER INFORMATION: n = A,T,C or G

<400> SEQUENCE: 10
tgacaccttc ctctaccagc tgccaggaac agtccagcca tgctcctcag cctcctcctc       60
ggcctcctcc acatcctcgt cctcagccac ctccctgcc tctgcctcct tcaagttcga      120
ggacttccag gtgtacggct gctacccgg cccctgagc ggcccagtgg atgaggcct         180 gtcctccagt ggctctgact actatggcag cccctgctcg gccccgtcgc cctccacgcc     240
cagcttccag ccgccccagc tctctccctg gctttgctga gctgtcaccg gctgaccagg     300
acctgttgct ggagtcggcc ttcctggagc tcttcatcct ccgcctggcg tacaggtcta     360
agccaggcga gggcaagctc atcttctgct cagcctggtg ctacaccggc tgcagtgtgc      420
ccgtggcttc ggggactgga ttgacagtat cctggccttc tcaaggtccc tgcacagctt      480
```

| | |
|---|---|
| gcttgtcgat gtccctgcct tcgcctgcct ctctgcccctt gtcctcatca ccgaccggca | 540 |
| tgggctgcan gagccgcggc gggtggagga gctgcagaac cgcatcgcca gctgcctgaa | 600 |
| ggagcacgtg gcagctgtgg cgggcgagcc ccagccagcc agctgcctgt cacgtctgtt | 660 |
| gggcanactg cccgagctgc ggaccctgtg caccccaggc ctgcagcgca tcttctacct | 720 |
| caagctggag g | 731 |

<210> SEQ ID NO 11
<211> LENGTH: 732
<212> TYPE: DNA
<213> ORGANISM: Homo sapiens
<220> FEATURE:
<221> NAME/KEY: misc_feature
<222> LOCATION: 1, 2, 664, 671, 717, 724, 731
<223> OTHER INFORMATION: n = A,T,C or G

<400> SEQUENCE: 11

| | |
|---|---|
| nncaggaatt cggcacgagt ctcactgtaa acattagctc tttccctgcc tacctggacc | 60 |
| ccagtctagg aattaaatct gcacctaacc aaggtccctt gtaagaaatg tccattcaag | 120 |
| cagtcattct ctgggtatat aatatgattt tgactacctt atctggtgtt aagatttgaa | 180 |
| gttggccttt tattggacta aaggggaact cctttaaggg tctcagttag cccaagtttc | 240 |
| ttttgcttat atgttaatag ttttaccctc tgcattggag agaggagtgc tttactccaa | 300 |
| gaagctttcc tcatggttac cgttctctcc atcatgccag ccttctcaac ctttgcagaa | 360 |
| attactagag aggatttgaa tgtgggacac aaaggtccca tttgcagtta gaaaatttgt | 420 |
| gtccacaagg acaagaacaa agtatgagct ttaaaactcc ataggaaact tgttaatcaa | 480 |
| caaagaagtg ttaatgctgc aagtaatctc tttttttaaaa cttttttgaag ctacttattt | 540 |
| tcagccaaat aggaatatta gagagggact ggtagtgaga atatcagctc tgtttggatg | 600 |
| gtggaaggtc tcattttatt gagattttta agatcatgca aaggtttgga aatagaacct | 660 |
| ctangccct nctcagtgtg ggtgggctga agttaaaga cagcgtggct gcagtancat | 720 |
| aaangcccta na | 732 |

<210> SEQ ID NO 12
<211> LENGTH: 869
<212> TYPE: DNA
<213> ORGANISM: Homo sapiens

<400> SEQUENCE: 12

| | |
|---|---|
| tgattcagtt tcctctacgg tatgagagac tggctcaaga atatcctcat gcagctttat | 60 |
| gaagccaact ctgaacacgc tggttatcta aatgagaagc agagaaataa agtcaagaaa | 120 |
| atttacctgg atgaaaagag cttttggct ggggaccatc ccattgacct tctcttaagg | 180 |
| gactttaaga aaaactacca catgtatgtg tatcctgtgc actggcagtt tagtgaactt | 240 |
| gaccaacacc ctatggatag agtcttgaca cattctgaac ttgctcctct gcgagcatct | 300 |
| ctggtgacca tggaacactg cataacccgt ttctttgagg agtgtgaccc caacaaggat | 360 |
| aagcacatca ccctgaagga gtggggccac tgctttggaa ttaaagaaga ggacatagat | 420 |
| gaaaatctct tgttttgaac gaagatttta agaactcaa ctttccagca tcctcctctg | 480 |
| ttctaaccac ttcagaaata tatgcagctg tgatacttgt agatttatat ttagcaaaat | 540 |
| gttagcatgt atgacaagac aatgagagta attgcttgac aacaacctat gcaccaggta | 600 |
| tttaacatta actttggaaa caaaaatgta caattaagta aagtcaacat atgcaaaata | 660 |
| ctgtacattg tgaacagaag tttaattcat agtaatttca ctctctgcat tgacttatga | 720 |

```
gataattaat gattaaacta ttaatgatta aaataatgca tttgtattgt tcataatatc    780
atgtgcactt taagaaaatg gaatgcttct ttttttgtgg tttacgtgta ttattttcaa    840
tattttaata ctttatttaa gatcctaaa                                      869
```

<210> SEQ ID NO 13
<211> LENGTH: 744
<212> TYPE: DNA
<213> ORGANISM: Homo sapiens

<400> SEQUENCE: 13

```
tagactcgga gggacatctc tacaccgttc ccatccggga acagggcaac atctacaagc     60
ccaacaacaa ggccatggca gacgagctga gcgagaagca agtgtacgac gcgcacacca    120
aggagatcga cctggtcaac cgcgacccta aacacctcaa cgatgacgtg gtcaagattg    180
actttgaaga tgtgattgca gaaccagaag ggacacacag ttttgacggc atttggaagg    240
ccagcttcac caccttcact gtgacgaaat actggtttta ccgcttgctg tctgccctct    300
ttggcatccc gatggcactc atctggggca tttacttcgc cattctctct ttcctgcaca    360
tctgggcagt tgtaccatgc attaagagct cctgattga gattcagtgc atcagccgtg     420
tctattccat ctacgtccac accgtctgtg acccactctt tgaagctgtt gggaaaatat    480
tcagcaatgt ccgcatcaac ttgcagaaag aaatataaat gacatttcaa ggatagaagt    540
atacctgatt tttttccctt ttaattttcc tggtgccaat ttcaagttcc aagttgctaa    600
tacagcaaca atttatgaat tgaattatct tggttgaaaa taaaaagatc actttctcag    660
ttttcataag tattatgtct cttctgagct atttcatcta ttttttggcag tctgaatttt    720 taaaaaccca tttaaatttt tttt                                           744
```

<210> SEQ ID NO 14
<211> LENGTH: 739
<212> TYPE: DNA
<213> ORGANISM: Homo sapiens
<220> FEATURE:
<221> NAME/KEY: misc_feature
<222> LOCATION: 719, 725, 727
<223> OTHER INFORMATION: n = A,T,C or G

<400> SEQUENCE: 14

```
acatttccac agggaaacag ctatgacatg attacgaatt taatacgact cactataggg     60
aatttggccc tcgaggccaa gaattcggca cgagcatcgt taacattgtg catgtgatcc    120
aggataacct catccgtaag gaagtttaca tcctcctaaa ttggataggc tatgtcaatt    180
ctggtttcaa tccccttatc tactgccgga gcccagattt caggattgcc ttccaggagc    240
ttctgtgcct gcgcaggtct tctttgaagg cctatgcaa tggctactcc agcaacggca     300
acacagggga gcagagtgga tatcacgtgg aacaggagaa agaaaataaa ctgctgtgtg    360
aagacctccc aggcacggaa gactttgtgg gccatcaagg tactgtgcct agcgataaca    420
ttgattcaca agggaggaat tgtagtacaa atgactcact gctataaagc agttttcta     480 cttttaaaga cccccccccg cccaacagaa cactaaacag actatttaac ttgagggtaa    540
taaacttaga ataaaattgt aaaattgtat agagatatgc agaaggaagg gcatccttct    600
gcctttttta tttttttaag ctgtaaaaag agagaaaact tatttgagtg attatttgtt    660
atttgtcagg tcagttcctc tttgcatgga atttgaagtt tatgtctaaa gagctttant    720
cctanangac ctgagtctg                                                 739
```

<210> SEQ ID NO 15

```
<211> LENGTH: 742
<212> TYPE: DNA
<213> ORGANISM: Homo sapiens
<220> FEATURE:
<221> NAME/KEY: misc_feature
<222> LOCATION: 665, 705, 722
<223> OTHER INFORMATION: n = A,T,C or G

<400> SEQUENCE: 15
caatttccac aggaaacagc tatgaccatg attacgccaa gcttggcacg aggaaacctt      60
gcaatatcag ctagatttac actccgggac gttgcccaaa ggtaggaaga aagcagaggg     120
aaatatttca gtcatcattt ccaaagtcat tatcaaaatc tgtgaggaag tttaatcttc     180
caaagagtca atgtcagaca tcaggcctct gttgcctgct tctctcgagg cactagatta     240
ggagtcttca ataagagact taacatgagg tatatggaag atgaggcacc gagataagtt     300
catcattagg tgtgagcact gctcacccct tgctggcaag tctccttaag ggcctgaagc     360
acaggtgtcc aaagaaaagc gttaagtcca tcttaataga atctatgtgg tatatgatgt     420
ggtcagcccc tggtctgtga tcagcaagaa cctacagcac agattatgcc ctgcccactt     480
caatgaatac ctactctcct ccattctcca tcacttttt tgctatcaag aactccggac       540
cttgcccatg gagaagttta agaggaact  cttgtggaga gctggtttat tttctgcctg     600
tgcgacgagt ttcagctggc caagaaagga gtcaagttat taaaaagcat cacaatgtag     660
atctncagct gggttttttgg tttttggtgg taaaactggg gaaangggc tatttattct     720 gncttaaatc aatggcaaat aa                                                742

<210> SEQ ID NO 16
<211> LENGTH: 718
<212> TYPE: DNA
<213> ORGANISM: Homo sapiens
<220> FEATURE:
<221> NAME/KEY: misc_feature
<222> LOCATION: 7, 27
<223> OTHER INFORMATION: n = A,T,C or G

<400> SEQUENCE: 16
caatttncac aggaaacagc tatgacnatg attacgccaa gcttggcacg aggcccagcc      60
cagcccagct cagctcagct actgccaagg gcaggaccaa tggctgagcc tcgtgtccag     120
actcagaggg ctggattttg gttcccttgt aaagacagag tgaatttcag tataaagatc     180
acccgttgta ttcaccccac acccagggct agtataaaca tgaccctggg ctttgtacca     240
cactagaatt catgtgagaa agctaaaatg gtggtcttct ccaccagccc ctcacaggct     300
tgggggtttt caatgtgaaa cacatgccag tttttaaaat gctgctttgt ccaggtgaga     360
acatccataa tttggggccc tgagttttac ccagactcaa ggagttggta aagggttaat     420
agccagatag tagaaccagt gaggagatgc ggccaaagat tctttatatc tgaaccaaga     480
tgtaaaacaa gaaatgcttt gaggctttct aagcgatcct cctgtctaat ttgcaccttt     540
gtctggatgc acacttctga ccttgctgcc acaacctgtg gggtctgatg tgtcccttga     600
tggggctgcc tcaaggactg cccctgcaag tgttaaagca catttctttt tttggccctg     660
ggcccaaacc aatgctgatg accctataac ttctgtttct tccatacttg catacccc       718

<210> SEQ ID NO 17
<211> LENGTH: 857
<212> TYPE: DNA
<213> ORGANISM: Homo sapiens

<400> SEQUENCE: 17
```

| | | | | |
|---|---|---|---|---|
| acaccaggct | tacctttta | agtttagtat | acagagacaa | ttttaatgga | aataactact | 60 |
| gtagactatt | gaagaatgat | ctctttgtga | tttaagaagt | ggctggattg | gaacttttaa | 120 |
| tatgctaatg | tggaaaatta | attaccttta | tgaaggtggt | ttattacaaa | taagcacact | 180 |
| aacccctcgg | aagttgtttt | acctacttta | aaagttttaa | tggattgcac | ctctgtaaac | 240 |
| tattcctaaa | atgtgtatga | tatatttgaa | aaggcttcca | ttaatataat | agctttgctt | 300 |
| gcagccttcc | aatctatgtt | ggtttacctg | tagtgtttta | taaagtgtgg | tcagaggccc | 360 |
| ctatagaatg | tattgtttga | aagtgtagtg | atatatttgt | gtttttattt | caagtaagtc | 420 |
| attttaaccg | aatgttcatt | catattcatt | tataaaaagt | acctgtatca | aaggaatttt | 480 |
| aacaaagagc | aatcagtatt | attggaccaa | atttggtgtt | tgttttcacc | ttgacgctct | 540 |
| tcttttcatt | atttctaatg | ctacaagaat | gctgttaagt | gtcttctaaa | atgatgtagc | 600 |
| ctgacaagac | attttttca | gtgtataaaa | ctaggtagta | ttgtgcactg | atttgaccat | 660 |
| tgtgaaatcc | tttctcagtg | taactgattt | tttaatttat | ttattgagtg | ataaatatta | 720 |
| aatattatat | tatttatttg | ttgttgtatg | cttatttctt | ttattgaggg | ttatttttat | 780 |
| tttggttttt | gctctttttt | ttctttgttt | tttattggta | tatttttttt | tttttcttaa | 840 |
| tttttttttt | tttttttt | | | | | 857 |

<210> SEQ ID NO 18
<211> LENGTH: 745
<212> TYPE: DNA
<213> ORGANISM: Homo sapiens
<220> FEATURE:
<221> NAME/KEY: misc_feature
<222> LOCATION: 508, 661, 731, 738
<223> OTHER INFORMATION: n = A,T,C or G

<400> SEQUENCE: 18

| | | | | |
|---|---|---|---|---|
| aggaattcgg | cacgagtctc | gatataacct | gacgatctca | gacgtcagcg | tgagtgatgt | 60 |
| gccatttcct | ttctctgccc | agtctggggc | tggggtgcca | ggctggggca | tcgcgctgct | 120 |
| ggtgctggtc | tgtgttctgg | ttgcgctggc | cattgtctat | ctcattgcct | tggctgtctg | 180 |
| tcagtgccgc | cgaaagaact | acgggcagct | ggacatcttt | ccagcccggg | atacctacca | 240 |
| tcctatgagc | gagtacccca | cctaccacac | ccatgggcgc | tatgtgcccc | ctagcagtac | 300 |
| cgatcgtagc | ccctatgaga | aggtttctgc | aggtaatggt | ggcagcagcc | tctcttacac | 360 |
| aaacccagca | gtggcagcca | cttctgccaa | cttgtagggg | cacgtcgccc | gctgagctga | 420 |
| gtggccagca | agtgccattc | cactccactc | aggttcttca | gggccagagc | ccctgcaccc | 480 |
| tgtttgggct | ggtgagctgg | gagttcangt | gggctgctca | cagcctcctt | caaaggcccc | 540 |
| accaatttct | cggacacttc | tcagtgtgtg | gaagctcatg | tgggcccctg | agggctcatg | 600 |
| cctgggaagt | ggtgtggtgg | gggctcccaa | gaagactggc | ccaaagagcc | ctgagatagc | 660 |
| ngggatcctg | aactggactg | aataaaacgt | gggcttccac | tgaaaaaaaa | aaaaaaaaa | 720 |
| aaaaactcga | nggggggncc | ggtcc | | | | 745 |

<210> SEQ ID NO 19
<211> LENGTH: 824
<212> TYPE: DNA
<213> ORGANISM: Homo sapiens
<220> FEATURE:
<221> NAME/KEY: misc_feature
<222> LOCATION: 219, 516, 538, 561, 581
<223> OTHER INFORMATION: n = A,T,C or G

<400> SEQUENCE: 19

```
catggggggcc tgcccagcat ctgagcaagg gtatgaagag atgagagctt ttcaggggcc    60
tggacatcag gccccccatg tccattatgc ccgcctaaaa actctacgta gcttagaggc   120
tacagactct gcctttgata accctgatta ctggcatagc aggcttttcc ccaaggctaa   180
tgcccagaga acgtaactcc tgctcccgt ggcactcang gagcatttaa tggcagctag    240
tgcctttaga gggtaccgtc ttctccctat tccctctctc tcccaggtcc cagccccttt   300
tccccagtcc cagacaattc cattcaatct tggaggctt taaacatttt tgacacaaaa   360
ttcttatggt atgtagccag ctgtgcactt tcttctcttt cccaacccca ggaaaggttt   420
tccttatttt gtgtgctttc ccagtcccat tcctcagctc cttcacaggc actcctggag   480
atatgaagga ttactctcca tatcccttcc tctcangctc ttgactactt ggaactangc   540
tcttatgtgt gcctttggtt nccatcagac tgtcaagaag nagaaaggaa gaaacctagc   600
agaggaagtg taatttggtt tatgactctt aaccccctag aagacagaag cttaaatctg   660
ggaagaagag gtaggagtag aattgattac tatcataatt cagcacttaa ctatgagcca   720
ggcatcatac taaacttcac ctacattatc tcacttaggc cttatcatcc ttaaaacaat   780
tcttgacata catattatct cattttacac aaaaggaagc cggc                   824

<210> SEQ ID NO 20
<211> LENGTH: 736
<212> TYPE: DNA
<213> ORGANISM: Homo sapiens
<220> FEATURE:
<221> NAME/KEY: misc_feature
<222> LOCATION: 599, 608, 623, 669, 678, 704, 706, 707, 714, 730
<223> OTHER INFORMATION: n = A,T,C or G

<400> SEQUENCE: 20
aatttacaca ggaaacagct atgacatgat tacgaattta atacgactca ctatagggaa    60
tttggccctc gaggccaaga attcggcacg agccctggag tacttggagg ggctggagtc   120
aagatagcgg ggccctggcc tggggcaccc actgcacact cagggccaga cccaccatcc   180
tggactggcg aggaagatca gtgcctcctg ctctgcccaa acacactccc atggggcaag   240
cactggagtg gatgctgggc tatcttgctc cccttccac tgtgggcagg ccttttcgct    300
tgtcccatgg gcgggtggtg ggccaaggag gagcttagca agtctgcagc ccagccccac   360
ctccataggg tcctgcaggc ctgtgctgag aggcctggtg ctgctgcaga gtgacaaagg   420
ctcaggacgg ctggctctgg gggactcaag ccaagcccct tggcaccatc ctggcttttg   480
gcagggatga gtgaggcccct gcagagagca tcccaagcca aggttccact cacctgcccc   540
ctctgcatgt gggtagagga tgtactggga cttggcatt aagattccat ctggcccanc    600
ccctgaangt cctggggaag cangtctaaa ttctgaataa ccagtggggc acactgactg   660
tcctcccang ggaactgnaa gggccttctt cccactgccc ctgnannccc tganatattt   720
tgttactatn cctccc                                                 736

<210> SEQ ID NO 21
<211> LENGTH: 690
<212> TYPE: DNA
<213> ORGANISM: Homo sapiens
<220> FEATURE:
<221> NAME/KEY: misc_feature
<222> LOCATION: 566, 571, 605, 643, 666, 680
<223> OTHER INFORMATION: n = A,T,C or G

<400> SEQUENCE: 21
cacgagagaa cttaccgatt gcttttctac cacgaactcc ttacttatga agcactggga    60
```

-continued

```
ctctgtccag aaggacaagg taacgctggt tgatagagga gataatacat atggaggaaa      120
gtgggtcata atcctagtg gtggactgat ttcaaaggga cacccactag gcgctacagg       180
tcttgctcag tgtgcagaac tctgctggca gctgagaggg gaagccggaa agaggcaagt     240
tcctggtgca aaggtggctc tgcagcataa tttaggcatt ggaggagctg tggttgtaac    300
actctacaag atgggttttc cggaagccgc cagttctttt agaactcatc aaattgaagc    360
tgttccaacc agctctgcaa gtgatggatt taaggcaaat cttgttttta aggagattga    420
gaagaaactt gaagaggaag gggaacagtt tgtgaagaaa atcggtggta tttttgcctt    480
caaggtgaaa gatggccctg ggggtaaaga ggccacctgg gtggtggatg tgaagaatgg    540
caaaggatca gtgcttccta actcanataa naaggctgac tgcacaatca caatggctga    600
ctcanacttc ctggctttaa tgactggtaa aatgaatcct cantcggcct tctttcaagg    660
caaatngaaa atcactggcn acatgggtct                                      690
```

<210> SEQ ID NO 22
<211> LENGTH: 811
<212> TYPE: DNA
<213> ORGANISM: Homo sapiens
<220> FEATURE:
<221> NAME/KEY: misc_feature
<222> LOCATION: 627, 634, 652, 662
<223> OTHER INFORMATION: n = A,T,C or G

<400> SEQUENCE: 22

```
gtaaaacaat agctatggac tttctattat ggaaaatgag attttttttt gatttagata      60
ttttacagtt tgtccgcctc acacatacac aatcatgcgc acacacacac acacaaaata    120
aagacacaca aggacgtctg cgcagcaaga aaagaatctc agttgccaag cagattgata    180
tcacacagac tcaaagcaaa ggcatgtgga acttctttat ttcaaaacag aagtgtctcc    240
ttgcacttag ccttggcaga cccttgactc caggggagat gacctgggga ggaagtgtgt    300
caactatttc tttaggcctg tttggctccg aagcctatat gtgcctggat cctctgccac    360
gggttaaatt ttcaggtgaa gagtgaggtt gtcatggcct cagctatgct tcctggctct    420
ccctcaagag tgcagccttg gctagagaac tcacagctct gggaaaaaga ggagcagaca    480
gggttccctg ggcccagtct cagcccagcc actgatgctg gatgaccttg gcctgaccct    540
ggtctggtct cagaatcact tttcccatct gtaaaattga gatgaatttg gtgttgaaag    600
ttcttcctgg agcagatgtc ctagaangtt ttangaatag tgacagagtc angccacccc    660
anaggccatg ggagccagct gacctgcttg accgaaggat ttctgacaga ctatctttgg    720
ggatgttttc aagaagggat ataagttatt tactttgggc atttaaaaga aaatttctct    780
cgggaataat ttatagaaaa ataaagcctc t                                    811
```

<210> SEQ ID NO 23
<211> LENGTH: 869
<212> TYPE: DNA
<213> ORGANISM: Homo sapiens
<220> FEATURE:
<221> NAME/KEY: misc_feature
<222> LOCATION: 510
<223> OTHER INFORMATION: n = A,T,C or G

<400> SEQUENCE: 23

```
atgtctaacc ctgctgccag tttatcacaa gtgcattaaa aatatagaga tctatcaagt       60
tccacattta tatgcaatca aactgaaaag gaccagacaa acagtgcaaa ggtcaaataa    120
ttactgtttt atattgggac agtacatttc agatttcaac caaaagacaa aaatgcagtt    180
```

```
taactcaaag gcacaacaat tgaaacacag aaaataatgg catctcttgg atgccttatt      240
tctaaattaa acaagaagt acacaaattt tgttcccttc cctcccccag tgcaagccca       300
caagcttttt ccaaagtctt gagcttttga tgctgtcccg cattgtggac ttgtgaggcg      360
cttggatgta gcaatgaaac aaaatgcttg agaggtctag tgaatggcat tcaaaaggga     420
cctcaaagtg cagacatatc tttttcaaat atgttacagg ctgaactggc tctttgaaca     480
ctatcactct gcttaaatcc agggaagcan gcttaaaaaa tgcaaaaggc atacaagttg    540
tatttcagtg caaatcttta gctggttatt ggaaaagatt ccaaaaatta aaaaaaaaa      600 aaaaaaatcc cttgtgtcac ctgccccctcc cccacccaa agccaaaatg aagaaaagac    660
agaacaaaaa aaaaaaaaaa aaaaaattgg cggccgcaag cttattcctt ttaatgaggg     720
ttaatttagc ctgccactgg ccggcggttt accaccgtcg gactgggaaa accctgcgtt    780
acccaactaa tcgccttgca gcacatcccc ctttggcagc tggcgtatta gcgaagaggc   840
ccggaccgat cgccttccc aacgttgat                                         869
```

<210> SEQ ID NO 24
<211> LENGTH: 735
<212> TYPE: DNA
<213> ORGANISM: Homo sapiens
<220> FEATURE:
<221> NAME/KEY: misc_feature
<222> LOCATION: 462, 463, 475, 639, 693, 728
<223> OTHER INFORMATION: n = A,T,C or G

<400> SEQUENCE: 24

```
caatttccac aggaaaacag ctatgacatg attacgaatt taatacgact cactataggg      60
aatttggccc tcgaggccaa gaattcggca cgaggttgac cgagctggag aaagccttga    120
actctatcat cgacgtctac cacaagtact ccctgataaa ggggaatttc catgccgtct    180
acagggatga cctgaagaaa ttgctagaga ccgagtgtcc tcagtatatc aggaaaaagg    240
gtgcagacgt ctggttcaaa gagttggata tcaacactga tggtgcagtt aacttccagg    300
agttcctcat tctggtgata aagatgggcg tggcagccca caaaaaaagc catgaagaaa    360
gccacaaaga gtagctgagt tactgggccc agaggctggg cccctggaca tgtacctgca   420
gaataataaa gtcatcaata cctcaaaaaa aaaaaaaaa annaaaaaaa aaaanggatc    480
tttaattaag cggccgcaag cttattccct ttagtgaggg ttaattttag cttggcactg    540
gccgtcgttt tacaacgtcg tgactgggaa acctgcgt tacccaactt aatcgccttg     600
cagcacatcc ccctttcgcc agctggcgta ataacgaana agcccgcacc gatcgccttc   660
caacagttgc gcacctgaat ggcgaatggg acnccctgt accggcgcat taaaccccgg    720
gggtggtngg gtcct                                                       735
```

<210> SEQ ID NO 25
<211> LENGTH: 818
<212> TYPE: DNA
<213> ORGANISM: Homo sapiens

<400> SEQUENCE: 25

```
aggagtgaga atcatagctg agcccggcag atactatgtt gcatcagctt tcacgcttgc      60
agttaatatc attgccaaga aaattgtatt aaaggaacag acgggctctg atgacgaaga   120
tgagtcgagt gagcagacct ttatgtatta tgtgaatgat ggcgtctatg gatcatttaa   180
ttgcatactc tatgaccacg cacatgtaaa gccccttctg caaaagagac ctaaaccaga    240
tgagaagtat tattcatcca gcatatgggg accaacatgt gatggcctcg atcggattgt   300
```

```
tgagcgctgt gacctgcccg aaatgcatgt gggtgattgg atgctctttg aaaacatggg      360
cgcttacact gttgctgctg cctctacgtt caatggcttc cagaggccga cgatctacta      420
tgtgatgtca gggcctgcgt ggcaactcat gcagcaattc cagaaccccg acttcccacc      480
cgaagtagag gaacaggatg ccagcaccct gcctgtgtct tgtgcctggg agagtgggat      540
gaaacgccac agagcagcct gtgcttcggc tagtattaat gtgtagatag cactctggta      600
gctgttaact gcaagtttag cttgaattaa aggatttggg gggaccatgt aacttaatta      660
ctgctagttt tgaaatgtct tgtaagagt agggtcgtca tgatgcagcc atatgaaaga       720
ctaggatatg gtcacactta tctgtgttcc tatgtaacta ttgtatattg ttttatatgg      780
attttattac tcttcaaacc gcttcttagt atgcccctt                             818

<210> SEQ ID NO 26
<211> LENGTH: 716
<212> TYPE: DNA
<213> ORGANISM: Homo sapiens
<220> FEATURE:
<221> NAME/KEY: misc_feature
<222> LOCATION: 1, 560, 650, 652, 706
<223> OTHER INFORMATION: n = A,T,C or G

<400> SEQUENCE: 26
naagccaaga attcggcacg agggttataa acgagaacgt gtgccattgt tttgacacag       60
gatttcttaa tagtgattag taaaggagcc caagaatgca caaagacaag agaatttgag      120
aggtttcagg agatgtgtta caaggcttat ctagctattc gacagcatgc caatctcttc      180
ataaatcttt tctcaatgat gcttggctct ggaatgccag aactacaatc ttttgatgac      240
attgcataca ttcgaaagac cctagcctta gataaaactg agcaagaggc tttggagtat      300
ttcatgaaac aaatgaatga tgcacatcat ggtggctgga caacaaaaat ggattggatc      360
ttcccacaat taaacagcat gcattgaact gaaaagataa ctgagaaaat gaaagctcac      420
tctggattcc acactgcact gttaataact ctcagcaggc aaagaccgat tgcataggaa      480
ttgcacaatc catgaacagc attagaattt acagcaagaa cagaaataaa atactatata      540
atttaaataa tgtaaacgcn aacagggttt gatagcactt aaactagttc atttcaaaat      600
taagctttaa aataatgcgc aatttcatgt tatgccttaa gtccaaaaan gnaaactttg      660
aagaatggtt gtatcttttt tttaaaaaca aacaaaaca aaaatnccccc aaatat         716

<210> SEQ ID NO 27
<211> LENGTH: 799
<212> TYPE: DNA
<213> ORGANISM: Homo sapiens
<220> FEATURE:
<221> NAME/KEY: misc_feature
<222> LOCATION: 466, 690
<223> OTHER INFORMATION: n = A,T,C or G

<400> SEQUENCE: 27
ttctgcgtgt ctctgcctga cacctactac ctgaagacct tcacgtctgc gtccaacaat       60
gagacctact gccggtcctt ctaccccgag cacagcatca aggagtggct gatcggcatg      120
gagctggtct ccgttgtctt gggctttgcc gttcccttct ccattatcgc tgtcttctac      180
ttcctgctgg ccagagccat ctcggcgtcc agtgaccagg agaagcacag cagccggaag      240
atcatcttct cctacgtggt ggtcttcctt gtctgctggt tgccctacca cgtggcggtg      300
ctgctggaca tcttctccat cctgcactac atccctttca cctgccggct ggagcacgcc      360
ctcttcacgg ccctgcatgt cacacagtgc ctgtcgctgg tgcactgctg cgtcaaccct      420
```

| | |
|---|---|
| gtcctctaca gcttcatcaa tcgcaactac aggtacgagc tgatgnaagc cttcatcttc | 480 |
| aagtactcgg ccaaaacagg gctcaccaag ctcatcgatg cctccagagt ctcagagacg | 540 |
| gagtactctg ccttggagca gagcaccaaa tgatctgccc tggagaggct ctggggacgg | 600 |
| gtttacttgt ttttgaacag ggtgatgggc ccctattgtt tctagagcaa agcaaagtag | 660 |
| cttcgggtct tgatgcttga gtagagtgan gaggggagca cgtgccccct gcatccattc | 720 |
| tctctttctc ttgatgacgc agctgtcatt tggctgggcg tgctgacagt ttgcaacagg | 780 |
| cagactgtgt cgcacagca | 799 |

<210> SEQ ID NO 28
<211> LENGTH: 739
<212> TYPE: DNA
<213> ORGANISM: Homo sapiens
<220> FEATURE:
<221> NAME/KEY: misc_feature
<222> LOCATION: 541, 729
<223> OTHER INFORMATION: n = A,T,C or G

<400> SEQUENCE: 28

| | |
|---|---|
| gaggaaacca ttgaccgcga gacttctggc aatttagagc aactactcct tgctgttgtg | 60 |
| aaatctattc gaagtatacc tgcctacctt gcagagaccc tctattatgc tatgaaggga | 120 |
| gctgggacag atgatcatac cctcatcaga gtcatggttt ccaggagtga gattgatctg | 180 |
| tttaacatca ggaaggagtt taggaagaat tttgccacct ctctttattc catgattaag | 240 |
| ggagatacat ctggggacta taagaaagct cttctgctgc tctgtggaga agatgactaa | 300 |
| cgtgtcacgg ggaagagctc cctgctgtgt gcctgcacca ccccactgcc ttccttcagc | 360 |
| acctttagct gcatttgtat gccagtgctt aacacattgc cttattcata ctagcatgct | 420 |
| catgaccaac acatacacgt catagaagaa aatagtggtg cttctttctg atctctagtg | 480 |
| gagatctctt tgactgctgt agtactaaag tgtacttaat gttactaagt ttaatgcctg | 540 |
| nccatttttcc atttatatat attttttaag aggctagagt gctttaagcc ttttttaaaaa | 600 |
| ctccattaat ataacattgg taaccatgat actttaatca gaagctttag cctgaaattg | 660 |
| gggaactctt ggaaatgtta ttagtgaagt tcgcaactaa actaaaccct gtaaattatg | 720 |
| atgattgcna tcaaaagat | 739 |

<210> SEQ ID NO 29
<211> LENGTH: 805
<212> TYPE: DNA
<213> ORGANISM: Homo sapiens
<220> FEATURE:
<221> NAME/KEY: misc_feature
<222> LOCATION: 711, 722, 727, 754, 800
<223> OTHER INFORMATION: n = A,T,C or G

<400> SEQUENCE: 29

| | |
|---|---|
| ttcccattaa gtggacagcg ccagaagcca ttaactacgg gacattcacc atcaagtcag | 60 |
| atgtgtggtc ttttgggatc ctgctgacgg aaattgtcac ccacggccgc atcccttacc | 120 |
| cagggatgac caacccggag gtgattcaga acctggagcg aggctaccgc atggtgcgcc | 180 |
| ctgacaactg tccagaggag ctgtaccaac tcatgaggct gtgctggaag agcgcccag | 240 |
| aggaccggcc caccttgac tacctgcgca gtgtgctgga ggacttcttc acggccacag | 300 |
| agggccagta ccagcctcag ccttgagagg ccttgagagg ccctggggtt ctccccttt | 360 |
| ctctccagcc tgacttgggg agatggagtt cttgtgccat agtcacatgg cctatgcaca | 420 |
| tatggactct gcacatgaat cccacccaca tgtgacacat atgcaccttg tgtctgtaca | 480 |

```
cgtgtcctgt agttgcgtgg actctgcaca tgtcttgtac atgtgtagcc tgtgcatgta    540
tgtcttggac actgtacaag gtacccctt ctggctctcc catttcctga gaccacagag     600
agagggagaa agcctggatt gacagaagct tctgcccacc tactttctt tcctcagatc     660 atccagaagt tcctcaaggc cagactttat ctaatacctc gtgtgctcct nctggtgcct    720
gncctgncac acatcagagt tcaataaatg tctngtgatg actgttaaaa aaaaaaaaa    780 aaaaaaaaat tggcggccgn aagct                                          805

<210> SEQ ID NO 30
<211> LENGTH: 722
<212> TYPE: DNA
<213> ORGANISM: Homo sapiens
<220> FEATURE:
<221> NAME/KEY: misc_feature
<222> LOCATION: 518, 534, 579, 608, 614, 622, 625, 668, 720
<223> OTHER INFORMATION: n = A,T,C or G

<400> SEQUENCE: 30
gaattgtgta ccgggccccc cctcgagact aactttagaa atacgggttt tgacttaact     60
cacaagagaa ctcatcataa gtacttgctg atggaagaat gacctagttg ctcctctcaa    120
catgggtaca gcaaactcag cacagccaag aagcctcagg tcgtggagaa catggattag    180
gatcctagac tgtaaagaca cagaagatgc tgacctcacc cctgccacct atcccaagac    240
ctcactggtc tgtggacagc agcagaaatg tttgcaagat aggccaaaat gagtacaaaa    300
ggtctgtctt ccatcagacc cagtgatgct gcgactcaca cgcttcaatt caagacctga    360
ccgctagtag ggaggtttat tcagatcgct ggcagcctcg gctgagcaga tgcacagagg    420
ggatcactgt gcagtgggac caccctcact ggccttctgc agcagggttc tgggatgttt    480
tcagtggtca aaatactctg tttagagcaa gggctcanaa aacagaaata ctgncatgga    540
ggtgctgaac acagggaaag tctggtccat attgggaant atgagcagaa caaatctcac    600
ttaatgcnca agtntaagtg tnccntgtct aacccatgtt gtatcaaata attttgtgcc    660
ataatgantc gaattttaac ataaaaaaaa ctctgccgat tctgcgcccg gggatcctan    720
tt                                                                   722

<210> SEQ ID NO 31
<211> LENGTH: 726
<212> TYPE: DNA
<213> ORGANISM: Homo sapiens
<220> FEATURE:
<221> NAME/KEY: misc_feature
<222> LOCATION: 698
<223> OTHER INFORMATION: n = A,T,C or G

<400> SEQUENCE: 31
aggattcggc acgagccaac tgttataggt tgttggataa atcagtggtt atttagggaa     60
ctgcttgacg taggaacggt aaatttctgt gggagaattc ttacatgttt tctttgcttt    120
aagtgtaact ggcagttttc cattggttta cctgtgaaat agttcaaagc caagtttata    180
tacaattata tcagtcctct ttcaaaggta gccatcatgg atctgtgtagg gggaaaatgt    240 gtattttatt acatctttca cattggctat ttaaagacaa agacaaattc tgtttcttga    300
gaagagaata ttagctttac tgtttgttat ggcttaatga cactagctaa tatcaataga    360
aggatgtaca tttccaaatt cacaagttgt gtttgatatc caaagctgaa tacattctgc    420
tttcatcttg gtcacataca attatttta cagttctccc aagggagtta ggctattcac    480
aaccactcat tcaaaagttg aaattaacca tagatgtaga taaactcaga aatttaattc    540
```

```
atgtttctta aatgggctac tttgtcctttt ttgttattag ggtggtattt aagtctatta      600
gccacaaaat tgggaaagga gtagaaaaag cagtaactga caacttgaat aatacaccag      660
agataatatg agaatcagat catttcaaaa ctcatttnct atgtaactgc attgagaact      720
gctatg                                                                726
```

<210> SEQ ID NO 32
<211> LENGTH: 836
<212> TYPE: DNA
<213> ORGANISM: Homo sapiens

<400> SEQUENCE: 32

```
attcatgcag atccaaagc tcttgctttg taatccaaga aaacaggggc ccgaaaccca       60
aggcagtaca gcagaattaa ttacagggct cgtccaactg gtccctcagt cacacatgcc     120
agagattgct caggaagcaa tggaggctct gctggttctt catcagttag atagcattga     180
tttgtggaat cctgatgctc ctgtagaaac attttgggag attaggtata tgtacttta      240 ttttttaaat tcaacttta aattttattt tgtattttg tcttgaaata ttaactctgt       300
agtacttagt acatgtaaaa cttacacttc caaaggtttt atggttttgt attttatttg     360
acttcaaatt attaggaatt tcttgtttta actgtaagaa aagtatcaca gcaatttag      420 aaataaattt taagaatagt gctaaatttt gtcaccccta acataagtac tgttgtttgg    480
tatattactt ttttcagatt tcaatgtggt tactactgta tttttaatag attttcatag    540
ttataagcct agaatgataa aatttttgtaa caatactgtt ttttcagttt tttgaactat    600
gatctttcat aaactttctg taataccaat gctttcgatg aatgaattaa taatggacac    660
ctgcttagaa gaaaaaatgt atgcagaatt tggggtctgc ttcctagatt atacaaatca    720 ttacattta atgagcatga agtcaccaca cgggagaaaa tgtaaatgtg taaacctcaa     780
gttgccatta tcttataaga atggtgtgct aagttactgg cagctgaaat aaccct        836
```

<210> SEQ ID NO 33
<211> LENGTH: 852
<212> TYPE: DNA
<213> ORGANISM: Homo sapiens
<220> FEATURE:
<221> NAME/KEY: misc_feature
<222> LOCATION: 464, 676, 684, 692, 697, 754, 790, 791, 802, 803, 823
<223> OTHER INFORMATION: n = A,T,C or G

<400> SEQUENCE: 33

```
cgccaagctt ggcacgaggg gaattccatg tcagcgttgg gattctcagt atcctcacga      60
gcatgacatg actcctgaaa atttcaagtg caaggaccta cgagaaaatt actgccgaaa     120
tccagatggg tctgaatcac cctggtgttt taccactgat ccaaacatcc gagttggcta    180
ctgctcccaa attccaaact gtgatatgtc acatggacaa gattgttatc gtgggaatgg    240
caaaaattat atgggcaact tatcccaaac aagatctgga ctaacatgtt caatgtggga    300
caagaacatg gaagacttac atcgtcatat cttctgggaa ccagatgcaa gtaagctgaa    360
tgagaattac tgccgaaatc cagatgatga tgctcatgga ccctggtgct acacgggaaa    420
tccactcatt ccttgggatt attgccctat ttctcgttgt gaangtgata ccacacctac    480
aatagtcaat ttagaccatc ccgtaatatc ttgtgccaaa acgaaacaat tgcgagttgt    540
aaatgggatt ccaacacgaa caaacatagg atggatggtt agtttgagat acagaaataa    600
acatatctgc ggagatcatt gataaaggag aagtggttct tactgcacga cagtgtttcc    660
cttctcgaga cttganagat tatngaagct gncttgnaat tcatgatgtc cacggaaaga    720
```

```
gagatgagaa atgcaaaaca gttctcaatg tttnccagct ggtatatggg ccoctgagga      780 tcagatctgn ntttaatgaa gnnctgccag cctgctgtcc tgnatgattt tgtagtacga      840
aatgattacc ta                                                          852
```

<210> SEQ ID NO 34
<211> LENGTH: 869
<212> TYPE: DNA
<213> ORGANISM: Homo sapiens

<400> SEQUENCE: 34

```
ctacttcaaa agcatctagt tgtagctgaa aaggttttgt tttattatat agttcttcat       60
agaggagacg ccacttgtta atttcttcag ttaattctgc tgttgtattt tcttttttcag     120 cttttcttcc ttcttcatct tccagctgtt ttctaaagtc ttcctcctgt tgcttgagtt     180
ggttctgcaa atcagttatt ttttgaagaa aagaaactgt gatttcttta atttctgttt     240
cctttagtgc tgacttggtc tgcagatcta aagcatcct tacatattct tgatttgagc      300
tctcagttgc caaaatctga tgctgaacat cctctgcatt tttcccagcc ttggccgctt     360
tttcctgtaa tgatgagttc tccagcttaa gatcttctat ctcactggct gttaacgctt     420
tatagctttc aaattgagca gtaacatctt caaggctttg caccatactg tcatactttt     480
cctgcaaaag cagggtggcc tgggtatgag cagcactact tttctccagt tcagcctccc     540
tccctttcag cttttcttct aggagtttta attcttcagc tctagatttt gcttcctctt     600
ccaattgctt gaccagcctt tcagcttgtt cctccttttg ctgtaattta tcaagctcat     660
ccagtgtttg ctttaattcc cctcaaaaaa aaaaaaaaa aaagatcttt aattaagcgg      720
ccgcaagctt attcccttaa ggagggttaa tttaggctgg cactggccgt cgttttacaa     780
cgacgggact gggaaaaccc tggcgtaccc aacttaatcg ccttgcagca catccccttt     840
tggcagctgg cgtaatagcg aaaaggtct                                        869
```

<210> SEQ ID NO 35
<211> LENGTH: 848
<212> TYPE: DNA
<213> ORGANISM: Homo sapiens
<220> FEATURE:
<221> NAME/KEY: misc_feature
<222> LOCATION: 657, 803, 804, 810, 813, 846
<223> OTHER INFORMATION: n = A,T,C or G

<400> SEQUENCE: 35

```
cctgaggggc tacgatttac cagaacacat cagcaatcca gaagattacc acagatctat       60
ccgccattcc tctattcaag aatgaaaaat gtcaagatga gtggttttct ttttcctttt     120 ttttttttt ttttgatacg gagatacggg gtcttgctct gtctcccagg ctggagtgca      180
gtgacacaat ctcagctcac tgtgacctcc gcctcctggg ttcaagagac tcctgcct      240 cagctccctg gtagctggga ttacaggtgt gagccactgc acccacccaa gacaagtgat     300
tttcattgta aatatttgac tttagtgaaa gcgtccaatt gactgccctc ttactgtttt     360
gaggaactca gaagtggaga tttcagttca gcggttgagg agaattgcgg cgagacaagc     420
atggaaaatc agtgacatct gattggcaga tgagcttatt tcaaaggaa gggtggcttt     480 gcatttcttg tgttctgtag actgccatca ttgatgatca ctgtgaaaat tgaccaagtg     540
atgtgtttac atttactgaa atgcgctctt taatttgttg tagattaggt cttgctggaa     600
gacagagaaa acttgccttt cagtattgac actgactaga gtgatgactg cttgtangta     660
tgtctgtgcc atttctcagg gaaagtagaa tgtaaatgaa gaagcctcac acgtaaaaga     720
```

| | |
|---|---|
| aatgtattaa cgtatgtagg agctggcagt cttgggggaaa gacactggct gagggaaaga | 780 |
| aatgaatctt tgactgaagc cgnngcctgn agncctgggg agcccatcc cccacctgcc | 840 |
| agcggntt | 848 |

<210> SEQ ID NO 36
<211> LENGTH: 848
<212> TYPE: DNA
<213> ORGANISM: Homo sapiens
<220> FEATURE:
<221> NAME/KEY: misc_feature
<222> LOCATION: 601
<223> OTHER INFORMATION: n = A,T,C or G

<400> SEQUENCE: 36

| | |
|---|---|
| cgccaagctt ggcacgaggc cattccattg ttcattcttc tttcttgaaa tcccaaacct | 60 |
| tctattaaca tttcttttca gttatacact gaactttact gtagcctttc ttctagagta | 120 |
| acaaatgttc tttgttttcc ttcctctaaa gatgtcttta tgtttccttc attcccaaag | 180 |
| aatattttg tggaatataa gattcagagt tggcagttgt tttcttttag acttcagaga | 240 |
| tgtatctctc tgttctgtac attattgttt aatataagaa acctactacc attcaaataa | 300 |
| tcattcccta ttttacaatg catcagttct gtcaagcttc attcaaagtg tttttcattg | 360 |
| tctctagtgt tcagaagttt ggctgtgatg tgcgtggcat ggaagttttt gggtgtattc | 420 |
| tatttggcgc tccctggtgc ttgcccagct ttttgatctg taggattatg ccttttgcaa | 480 |
| aatttgggga actttcaact attatttctt caaatatttt ttcaccccc agtcttgtct | 540 |
| tttttaggga cttcaataac atgagtggca gatcttgttt tacactccca tgggtccttc | 600 |
| nagctctcat cttttttctt tttccagtct attttctgtc ttgttaatat tgattaattt | 660 |
| ttattgacct tccatggtcc tcactgattg ttttctttgt catacctaat ctgttgagtt | 720 |
| tgtgcagtga gttttcattt tggtttgtat tttccagttg tttaatttcc attgggtggg | 780 |
| ttcttttgta caccttctgt ttctttgctt atttttttaac gccaaaagaa gactctcaga | 840 |
| gaatagac | 848 |

<210> SEQ ID NO 37
<211> LENGTH: 820
<212> TYPE: DNA
<213> ORGANISM: Homo sapiens
<220> FEATURE:
<221> NAME/KEY: misc_feature
<222> LOCATION: 547, 691
<223> OTHER INFORMATION: n = A,T,C or G

<400> SEQUENCE: 37

| | |
|---|---|
| tgcatgatat tgttctccaa gggatgggaa tcaggcatgt gtcccttcca agctgtgtta | 60 |
| actgttcaaa ctcaggcctg tgtgactcca ttggggtgag aggtgaaagc ataacatggg | 120 |
| tacagagggg acaacaatga atcagaacag tatgctgagc cataggtcta aataggatcc | 180 |
| tggaggctgc ctgctgtgct gggaggtata ggggtcctgg gggcaggcca ggcagttga | 240 |
| caggtacttg gagggctcag ggcagtggct tctttccagt atggaaggat ttcaacattt | 300 |
| taatagttgg ttaggctaaa ctggtgcata ctggcattgg cccttggtgg ggagcacaga | 360 |
| cacaggatag gactccattt cttttcttcca ttccttcatg tctaggataa cttgcttct | 420 |
| tctttccttt actcctggct caagccctga atttcttctt ttcctgcagg ggttgagagc | 480 |
| tttctgcctt agcctaccat gtgaaactct accctgaaga aagggatgga taggaagtag | 540 |
| acctctnttt cttaccagtc tcctccccta ctctgcccct aagctggctg tacctgttcc | 600 |

| | |
|---|---|
| tccccccataa aatgatcctg ccaatctaat gtgagtgtga agctttgcac actagtttat | 660 |
| gctacctagt ctccactttc tcaatgctta ngagacagat cactcctgga ggctggggat | 720 |
| ggtaggattg ctggggattt ttttttttaa acagggtctc actctgttgc ccaggctagt | 780 |
| gagctgggat catgcccatg cactccagcc taagtgacag | 820 |

<210> SEQ ID NO 38
<211> LENGTH: 602
<212> TYPE: DNA
<213> ORGANISM: Homo sapiens
<220> FEATURE:
<221> NAME/KEY: misc_feature
<222> LOCATION: 355, 506, 523, 578, 581
<223> OTHER INFORMATION: n = A,T,C or G

<400> SEQUENCE: 38

| | |
|---|---|
| atgggaacga tattctcgaa aggtgtttgt aggcggattg cctccagaca ttgatgaaga | 60 |
| tgagatcaca gctagttttc gtcgctttgg ccctcttgat tgtggattgg cctcataaag | 120 |
| ctgagagcaa atcctatttt cctcctaaag ctatgcatt cctgctgttt caagatgaaa | 180 |
| gctctgtgca ggctctcatt gatgcatgca ttgaagaaga tggaaaactc tacctttgtg | 240 |
| tatcaagtcc cactatcaag ataagccag tccagattcg gccttggaat ctcagtgaca | 300 |
| gtgactttgt gatggatggt tcacagccac ttgacccacg aaaaactata tttgntggtg | 360 |
| gtgttcctcg accattacga gctgtggagc ttgcgatgat aatggatcgg ctatatggag | 420 |
| gtgtgtgcta cgctgggatt gataccgacc ctgagctaaa atacccaaaa ggagctggga | 480 |
| gagttgcgtt ctctaatcaa cagagntaca taactgctat cantgccccc tttgttcaac | 540 |
| tgcagcatgg agagaaagat aaacgggggg aagttaancc ntatgtcttg gatgaacaac | 600 |
| tg | 602 |

<210> SEQ ID NO 39
<211> LENGTH: 731
<212> TYPE: DNA
<213> ORGANISM: Homo sapiens
<220> FEATURE:
<221> NAME/KEY: misc_feature
<222> LOCATION: 26, 640, 645, 671
<223> OTHER INFORMATION: n = A,T,C or G

<400> SEQUENCE: 39

| | |
|---|---|
| aatttacaca ggaaacagct atgacntgat tacgccaagc ttggcacgag ggcaaatcaa | 60 |
| gagaaactct gcagggcact cccctgtttc ctaagaacga aaaagtgcaa taaaggccat | 120 |
| tcgttaccta cttttcagca gcccacaaga tgtagcacta ttagtgtccc cctcagaggc | 180 |
| ttaatgttgc ctgtggagca gtgccatcc cagcccgttt ctgccacca gttgttctca | 240 |
| ggaaccttac ccatgctcca gcgtccttca cctggcacag acatgcaag ataaataggg | 300 |
| caggcacgtg tttgggtgtc ctctcttttc tgataaaatc catcccgtgt ttgccacacg | 360 |
| ccctccagtc ctcagttccc actgcctaac gtctgccccc gtgtagatac tgagaggtgg | 420 |
| tggcagtaat tgtggcctta tcagccgctc agttccaggc ttttgcccag gtcactgttg | 480 |
| ccccatgttc ggagaacctg gccacctgtc ttggctttct catccttccc aacccagtgc | 540 |
| cgtttatttc agaagcttct ggcactgggc ttggatgctt cgggcttctg actgctccat | 600 |
| aagttttgac tggtgaaaca agggcccaga tgacaacctn tcttngcttc acaagtacgc | 660 |
| gggagcctca ngttctctca agggcagcaa aagtggccca agctggcccc tgacagcaca | 720 |
| agggcctggg g | 731 |

```
<210> SEQ ID NO 40
<211> LENGTH: 770
<212> TYPE: DNA
<213> ORGANISM: Homo sapiens
<220> FEATURE:
<221> NAME/KEY: misc_feature
<222> LOCATION: 449, 584, 641, 696, 762
<223> OTHER INFORMATION: n = A,T,C or G

<400> SEQUENCE: 40
aggacgctgg gactcagcag cccatgtgta caacagggtt ccagcacagc agctgtattt      60
taccacccct tccaaccaga atgtatacca ggtggactct ctgcaatcta cgtgaaagac     120
cccacacccc tccttgctgg aatgtgtctg gcccttcagc agtttctctt ggcagcatca     180
gctgggctgc tttctttgtg tgtggcccca ggtgtcaaaa tgacaccagc tgtctgtact     240
agacaaggtt accaagtgcg gaattggtta atactaacag agagatttgc tccattctct     300
ttggaataac aggacatgct gtatagatac aggcagtagg tttgctctgt acccatgtgt     360
acagcctacc catgcaggga ctgggattcg aggacttcca ggcgcatagg gtagaaccaa     420
atgatagggt aggagcatgt gttctttang gccttgtaag gctgtttcct tttgcatctg     480
gaactgacta tataattgtc ttcaatgaag aactaattca atttgcatat agaggagcca     540
aagagagatt tcagctctgt atttgtggta tcagtttgga aaanaaaatc tgatactcca     600
tttgattatt gtaaatattt gatcttgaat cacttgacag ngtttgtttg aattgtgttt     660 gttttttcctt tgatgggctt aaaagaaatt atccanaggg agaaagagca gcatgccact    720
tcttaaaaca gaaacaaaca aaaagaaaa atgcgctctt nctaatcca               770

<210> SEQ ID NO 41
<211> LENGTH: 725
<212> TYPE: DNA
<213> ORGANISM: Homo sapiens
<220> FEATURE:
<221> NAME/KEY: misc_feature
<222> LOCATION: 6, 549, 684, 709, 715, 724
<223> OTHER INFORMATION: n = A,T,C or G

<400> SEQUENCE: 41
catttncaca ggaaacagct atgaccatga ttacgccaag cttggcacga ggcatcattc      60
catttgccca cgccatctgg cacctgtttg tggccacggc agctgcagtg cattactacg     120
ccatttggaa ataccttttac cgaagtccta cggactttat gcggcattta tgaccaatct    180
gtactaattc tccaaaccag tattatttca attatgcac ttgggagtgg gggagagcta     240
aacattgcac agggaaagaa aaaaaataac tgcactgact ttatatcttt tgaatataat     300
tactgtgaaa gtataaaggc tgtgttctgg aattttctgc ctcacagcaa ataaataagg     360
tagtgaatta attattcatt ccattccact atcatgaagg actctgaata gacttggcca     420
actgatgttt acaaaccaga cttttatatt ttaattttac agattttact acatgatttt     480
tctaaattac tatgtcaggt tgtaaaagtc agtgcaataa caaaccttcc tttttaagaa     540
gaaaattgnt tctattactt tcccattcac taggtaaaga atcatggaca gaacttacac     600 tacttttttac catgtttcat cttggcataa catgggtctt ttttaaataa aaactttaat    660 ttttttgtaaa ttttttaaaaa aaanttcatt gatatgcatc tcttgaagnc ctcantcatg    720 tggna                                                                 725

<210> SEQ ID NO 42
<211> LENGTH: 845
<212> TYPE: DNA
```

<213> ORGANISM: Homo sapiens
<220> FEATURE:
<221> NAME/KEY: misc_feature
<222> LOCATION: 490, 572, 621
<223> OTHER INFORMATION: n = A,T,C or G

<400> SEQUENCE: 42

```
gtgagatttg tagcagaaag aggcaaacac tgtatacttg atgtatcagg aaatgctatc      60
aagcggttac aagttgccca gctctatccc attgccatct tcataaaacc caggtctctg     120
gaacctctta tggagatgaa taagcgtcta acagaggaac aagccaagaa aacctatgat     180
cgagcaatta agctagaaca agaatttgga gaatatttta cagctattgt ccaaggagat     240
actttagaag atatatataa ccaatgcaag cttgttattg aagagcaatc tgggcctttc     300
atctggattc cctcaaagga aaagttataa attagctact gcgcctctga caacgacaga     360
agagcattta gaagaacaaa atatatataa catactactt ggaggctttt atgttttttgt    420
tgcatttatg ttttttgcagt caatgtgaat tcttacgaat gtacaacaca aactgtatga    480
agccatgaan gaaaacagag ggccaaaggg tgggacagaa aagacattgc agtatgaaga    540
aggctttggt ttgctcaaag tgccaggtgt anggatgaac ctctgacggg ctttctgccc    600
aagagatgag atgagagcct nctcacccca gcagatgtcc agagctgatt tagctgcaga    660
gctctctgtg tcttttgctt taagaaaaa atgccagcac tcgaacctca tcagccttcc     720
cattacccac atctgtaatt ggtacacttt gaatttttata actatgcaca tcttttgatt   780
tcttaaacag caaatgaaag aaagaaggaa aaagaaagg aatcccttttg gagacgacat    840
actat                                                                845
```

<210> SEQ ID NO 43
<211> LENGTH: 1867
<212> TYPE: DNA
<213> ORGANISM: Homo sapiens

<400> SEQUENCE: 43

```
ggttcgctgt ggcgggcgcc tgggccgccg gctgtttaac ttcgcttccg ctggcccata      60
gtgatctttg cagtgaccca gcagcatcac tgtttcttgg cgtgtgaaga taacccaagg    120
aattgaggaa gttgctgaga gagtgtgct ggagatgctc taggaaaaa ttgaatagtg      180
agacgagttc cagcgcaagg gtttctggtt tgccaagaag aaagtgaaca tcatggatca    240
gaacaacagc ctgccacctt acgctcaggg cttggcctcc cctcagggtg ccatgactcc    300
cggaatccct atctttagtc caatgatgcc ttatggcact ggactgaccc cacagcctat   360
tcagaacacc aatagtctgt ctattttgga agagcaacaa aggcagcagc agcaacaaca    420
acagcagcag cagcagcagc agcagcaaca gcaacagcag cagcagcagc agcagcagca    480
gcagcagcag cagcagcagc agcagcagca gcaacaggca gtggcagctg cagccgttca    540
gcagtcaacg tccagcagg caacacaggg aacctcaggc caggcaccac agctcttcca     600
ctcacagact ctcacaactg cacccttgcc gggcaccact ccactgtatc cctccccat    660
gactcccatg acccccatca ctcctgccac gccagcttcg gagagttctg ggattgtacc    720
gcagctgcaa aatattgtat ccacagtgaa tcttggttgt aaacttgacc taaagaccat    780
tgcacttcgt gcccgaaacg ccgaatataa tcccaagcgg tttgctgcgg taatcatgag    840
gataagagag ccacgaacca cggcactgat tttcagttct gggaaaatgg tgtgcacagg    900
agccaagagt gaagaacagt ccagactggc agcaagaaaa tatgctagag ttgtacagaa    960
gttgggtttt ccagctaagt tcttggactt caagattcag aatatggtgg ggagctgtga   1020
```

-continued

| | | | | |
|---|---|---|---|---|
| tgtgaagttt | cctataaggt | tagaaggcct | tgtgctcacc | caccaacaat ttagtagtta | 1080 |
| tgagccagag | ttatttcctg | gtttaatcta | cagaatgatc | aaacccagaa ttgttctcct | 1140 |
| tattttttgtt | tctggaaaag | ttgtattaac | aggtgctaaa | gtcagagcag aaatttatga | 1200 |
| agcatttgaa | aacatctacc | ctattctaaa | gggattcagg | aagacgacgt aatggctctc | 1260 |
| atgtacccct | gcctccccca | ccccttctt | tttttttttt | taaacaaatc agtttgtttt | 1320 |
| ggtaccttta | aatggtggtg | ttgtgagaag | atggatgttg | agttgcaggg tgtggcacca | 1380 |
| ggtgatgccc | ttctgtaagt | gcccaccgcg | ggatgccggg | aaggggcatt atttgtgcac | 1440 |
| tgagaacacc | gcgcagcgtg | actgtgagtt | gctcataccg | tgctgctatc tgggcagcgc | 1500 |
| tgcccattta | tttatatgta | gattttaaac | actgctgttg | acaagttggt ttgagggaga | 1560 |
| aaactttaag | tgtaaagcc | acctctataa | ttgattggac | ttttaattt taatgttttt | 1620 |
| ccccatgaac | cacagttttt | atatttctac | cagaaaagta | aaaatctttt ttaaaagtgt | 1680 |
| tgttttttcta | atttataact | cctagggggtt | atttctgtgc | cagacacatt ccacctctcc | 1740 |
| agtattgcag | gacagaatat | atgtgttaat | gaaaatgaat | ggctgtacat atttttttct | 1800 |
| ttcttcagag | tactctgtac | aataaatgca | gtttataaaa | gtgttaaaaa aaaaaaaaa | 1860 |
| aaaaaaa | | | | | 1867 |

<210> SEQ ID NO 44
<211> LENGTH: 2650
<212> TYPE: DNA
<213> ORGANISM: Homo sapiens

<400> SEQUENCE: 44

| | | | | |
|---|---|---|---|---|
| gctctgggag | tgtgaaactg | ggagagacgg | ttaagctggg | gacggtattc agaattcgag | 60 |
| cgcaggagct | ccgcttctcc | acctgctccc | ggggagctat | tgggatccag agaatcaccc | 120 |
| gctgatggtt | tttgcccagg | cctgaaacaa | ccagagagct | acgggaaagg aagggcttgg | 180 |
| cttgccagag | gaattttcca | agtgctcaaa | cgccaggctt | acggcgcctg tgatccgtcc | 240 |
| aggaggacaa | agtgggattt | gaagatccac | tccacttctg | ctcatggcgg gccagggcct | 300 |
| gccccctgcac | gtgccacac | tgctgactgg | gctgctggaa | tgcctgggct ttgctggcgt | 360 |
| cctctttggc | tggccttcac | tagtgtttgt | cttcaagaat | gaagattact ttaaggatct | 420 |
| gtgtggacca | gatgctgggc | cgattggcaa | tgccacaggg | caggctgact gcaaagccca | 480 |
| ggatgagagg | ttctcactca | tcttcaccct | ggggtccttc | atgaacaact tcatgacatt | 540 |
| ccccactggc | tacatctttg | accggttcaa | gaccaccgtg | gcacgcctca tagccatatt | 600 |
| tttctacacc | accgccacac | tcatcatagc | cttcacctct | gcaggctcag ccgtgctgct | 660 |
| cttcctggcc | atgccaatgc | tcaccattgg | gggaatcctg | tttctcatca ccaacctgca | 720 |
| gattgggaac | ctatttggcc | aacaccgttc | gaccatcatc | actctgtaca atggagcatt | 780 |
| tgactcttcc | tcggcagtct | tccttattat | taagcttctt | tatgaaaaag gcatcagcct | 840 |
| cagggcctcc | ttcatcttca | tctctgtctg | cagtacctgg | catgtagcac gcactttcct | 900 |
| cctgatgccc | cggggggcaca | tcccataccc | actgccccc | aactacagct atggcctgtg | 960 |
| ccctgggaat | ggcaccacaa | aggaagagaa | ggaaacagct | gagcatgaaa acagggagct | 1020 |
| acagtcaaag | gagttccttt | cagcgaagga | agagaccccca | ggggcagggc agaagcagga | 1080 |
| actccgctcc | ttctggagct | acgctttctc | tcggcgcttt | gcctggcacc tggtgtggct | 1140 |
| gtctgtgata | cagttgtggc | actacctctt | cattggcact | ctcaactcct tgctgaccaa | 1200 |
| catggccggt | ggggacatgg | cacgagtcag | cacctacaca | aatgcctttg ccttcactca | 1260 |

|                                                            |      |
| ---------------------------------------------------------- | ---- |
| gttcggagtg ctgtgtgccc cctggaatgg cctgctcatg gaccggctta aacagaagta | 1320 |
| ccagaaggaa gcaagaaaga caggttcctc cactttggcg gtggccctct gctcgacggt | 1380 |
| gccttcgctg ccctgacat ccctgctgtg cctgggcttc gccctctgtg cctcagtccc | 1440 |
| catcctccct ctccagtacc tcaccttcat cctgcaagtg atcagccgct ccttcctcta | 1500 |
| tgggagcaac gcggccttcc tcacccttgc tttcccttca gagcactttg caagctctt  | 1560 |
| tgggctggta tggccttgt cggctgtggt gtctctgctc cagttcccca tcttcaccct  | 1620 |
| catcaaaggc tcccttcaga atgacccatt ttacgtgaat gtgatgttca tgcttgccat | 1680 |
| tcttctgaca ttcttccacc cctttctggt atatcgggaa tgccgtactt ggaaagaaag | 1740 |
| tccctctgca attgcatagt tcagaagccc tcacttttca gccccgagga tggttttgtt | 1800 |
| catcttccac cacctttgag gacctcgtgt cccaaaagac tttgcctatc ccagcaaaac | 1860 |
| acacacacac acacacacac acacaaaata aagacacaca aggacgtctg cgcagcaaga | 1920 |
| aaagaatctc agttgccaag cagattgata tcacacagac tcaaagcaaa ggcatgtgga | 1980 |
| acttctttat ttcaaaacag aagtgtctcc ttgcacttag ccttggcaga cccttgactc | 2040 |
| caggggagat gacctggggg aggaagtgtg tcaactattt ctttaggcct gtttggctcc | 2100 |
| gaagcctata tgtgcctgga tcctctgcca cgggttaaat tttcaggtga agagtgaggt | 2160 |
| tgtcatggcc tcagctatgc ttcctggctc tccctcaaga gtgcagcctt ggctagagaa | 2220 |
| ctcacagctc tgggaaaaag aggagcagac agggttccct gggcccagtc tcagcccagc | 2280 |
| cactgatgct ggatgacctt ggcctgaccc tggtctggtc tcagaatcac ttttcccatc | 2340 |
| tgtaaaattg agatgaattt tggtgttgaa agttcttcct ggagcagatg tcctagaagg | 2400 |
| ttttaggaat agtgacagag tcaggccacc ccaagggcca tggagccag ctgacctgct   | 2460 |
| tgaccgaagg atttctgaca gactatcttt ggggatgttt tcaagaaggg atataagtta | 2520 |
| tttactttgg gcatttaaaa gaaaatttct ctcgggaata attttataga aaaataaagc | 2580 |
| ttctgtgtct aaggcaaaaa aaaaaaaaaa aaaaaaaaaa aaaaaaaaaa aaaaaaaaaa | 2640 |
| aaaaaaaaaa                                                        | 2650 |

<210> SEQ ID NO 45
<211> LENGTH: 2672
<212> TYPE: DNA
<213> ORGANISM: Homo sapiens

<400> SEQUENCE: 45

|                                                                  |     |
| ---------------------------------------------------------------- | --- |
| gcgaatgcga acctggcccg tgcggaaagg gcgcggagag ccccggcgcg gagcaggcgg |  60 |
| gggacggtat tcagaattcg agcgcaggag ctccgcttct ccacctgctc ccggggagct | 120 |
| attgggatcc agagaatcac ccgctgatgg ttttttgccca ggcctgaaac aaccagagag | 180 |
| ctacgggaaa ggaagggctt ggcttgccag aggaattttc caagtgctca acgccaggc  | 240 |
| ttacggcgcc tgtgatccgt ccaggaggac aaagtgggat ttgaagatcc actccacttc | 300 |
| tgctcatggc gggccagggc ctgcccctgc acgtggccac actgctgact gggctgctgg | 360 |
| aatgcctggg ctttgctggc gtcctctttg gctggccttc actagtgttt gtcttcaaga | 420 |
| atgaagatta ctttaaggat ctgtgtggac cagatgctgg gccgattggc aatgccacag | 480 |
| ggcaggctga ctgcaaagcc caggatgaga ggttctcact catcttcacc ctggggtcct | 540 |
| tcatgaacaa cttcatgaca ttccccactg gctacatctt tgaccggttc aagaccaccg | 600 |
| tggcacgcct catagccata tttttctaca ccaccgccac actcatcata gccttcaccct | 660 |
| ctgcaggctc agccgtgctg ctcttcctgg ccatgccaat gctcaccatt ggggaatcc  | 720 |

```
tgtttctcat caccaacctg cagattggga acctatttgg ccaacaccgt tcgaccatca    780
tcactctgta caatggagca tttgactctt cctcggcagt cttccttatt attaagcttc    840
tttatgaaaa aggcatcagc ctcagggcct ccttcatctt catctctgtc tgcagtacct    900
ggcatgtagc acgcactttc ctcctgatgc cccgggggca catcccatac ccactgcccc    960
ccaactacag ctatggcctg tgccctggga atggcaccac aaaggaagag aaggaaacag   1020
ctgagcatga aaacagggag ctacagtcaa aggagttcct ttcagcgaag gaagagaccc   1080
caggggcagg gcagaagcag gaactccgct ccttctggag ctacgctttc tctcggcgct   1140
ttgcctggca cctggtgtgg ctgtctgtga tacagttgtg gcactacctc ttcattggca   1200
ctctcaactc cttgctgacc aacatggccg gtggggacat ggcacgagtc agcacctaca   1260
caaatgcctt tgccttcact cagttcggag tgctgtgtgc ccctggaat ggcctgctca    1320
tggaccggct taaacagaag taccagaagg aagcaagaaa gacaggttcc tccactttgg   1380
cggtggccct ctgctcgacg gtgccttcgc tggccctgac atccctgctg tgcctgggct   1440
tcgccctctg tgcctcagtc cccatcctcc ctctccagta cctcaccttc atcctgcaag   1500
tgatcagccg ctccttcctc tatgggagca acgcggcctt cctcacccct gctttccctt   1560
cagagcactt tggcaagctc tttgggctgg tgatggcctt gtcggctgtg gtgtctctgc   1620
tccagttccc catcttcacc ctcatcaaag gctcccttca gaatgaccca ttttacgtga   1680
atgtgatgtt catgcttgcc attcttctga cattcttcca cccctttctg gtatatcggg   1740
aatgccgtac ttggaaagaa agtccctctg caattgcata gttcagaagc cctcactttt   1800
cagcccgag gatggttttg ttcatcttcc accacctttg aggacctcgt gtcccaaaag    1860
actttgccta tcccagcaaa acacacacac acacacacac acacaaaa taaagacaca     1920
caaggacgtc tgcgcagcaa gaaaagaatc tcagttgcca agcagattga tatcacacag   1980
actcaaagca aaggcatgtg gaacttcttt atttcaaaac agaagtgtct ccttgcactt   2040
agccttggca gacccttgac tccaggggag atgacctggg ggaggaagtg tgtcaactat   2100
ttctttaggc ctgtttggct ccgaagccta tatgtgcctg gatcctctgc cacgggttaa   2160
attttcaggt gaagagtgag gttgtcatgg cctcagctat gcttcctggc tctccctcaa   2220
gagtgcagcc ttggctagag aactcacagc tctgggaaaa agaggagcag acagggttcc   2280
ctgggcccag tctcagccca gccactgatg ctggatgacc ttggcctgac cctggtctgg   2340
tctcagaatc acttttccca tctgtaaaat tgagatgaat tttggtgttg aaagttcttc   2400
ctggagcaga tgtcctagaa ggttttagga atagtgacag agtcaggcca ccccaagggc   2460
catgggagcc agctgacctg cttgaccgaa ggatttctga cagactatct ttggggatgt   2520
tttcaagaag ggatataagt tatttacttt gggcatttaa aagaaaattt ctctcgggaa   2580
taattttata gaaaataaa gcttctgtgt ctaaggcaaa aaaaaaaaaa aaaaaaaaa    2640
aaaaaaaaaa aaaaaaaaa aaaaaaaaa aa                                  2672
```